(12) United States Patent
Lee et al.

(10) Patent No.: US 9,095,535 B2
(45) Date of Patent: Aug. 4, 2015

(54) GABA RELEASE-REGULATING AGENT IN CEREBELLUM

(75) Inventors: Changjoon Justin Lee, Seoul (KR); Soo-Jung Lee, Seoul (KR); Bo-Eun Yoon, Yongin-si (KR)

(73) Assignee: KOREA INSTITUTE OF SCIENCE AND TECHNOLOGY, Seoul (KR)

(*) Notice: Subject to any disclaimer, the term of this patent is extended or adjusted under 35 U.S.C. 154(b) by 27 days.

(21) Appl. No.: 13/389,981

(22) PCT Filed: Aug. 24, 2010

(86) PCT No.: PCT/KR2010/005653
§ 371 (c)(1),
(2), (4) Date: Apr. 24, 2012

(87) PCT Pub. No.: WO2011/025230
PCT Pub. Date: Mar. 3, 2011

(65) Prior Publication Data
US 2012/0214742 A1  Aug. 23, 2012

(30) Foreign Application Priority Data
Aug. 24, 2009  (KR) .................. 10-2009-0077979

(51) Int. Cl.
| | |
|---|---|
| A61K 49/00 | (2006.01) |
| A61P 25/00 | (2006.01) |
| A61P 25/28 | (2006.01) |
| A61P 25/32 | (2006.01) |
| A61P 25/08 | (2006.01) |

(Continued)

(52) U.S. Cl.
CPC ............. *A61K 31/00* (2013.01); *A61K 31/185* (2013.01); *A61K 31/196* (2013.01); *A61K 31/455* (2013.01); *A61K 31/713* (2013.01); *A61K 31/7105* (2013.01); *A61K 38/043* (2013.01); *A61K 38/08* (2013.01); *G01N 33/9426* (2013.01); *G01N 2500/10* (2013.01)

(58) Field of Classification Search
None
See application file for complete search history.

(56) References Cited

U.S. PATENT DOCUMENTS

2008/0103205 A1   5/2008   Bloomquist

FOREIGN PATENT DOCUMENTS

| KR | 10-2009-0083532 | | 3/2009 | |
|---|---|---|---|---|
| KR | WO2009096612 | * | 8/2009 | ............. A61K 48/00 |
| WO | WO2006062683 | * | 6/2006 | ........... A61K 31/533 |

OTHER PUBLICATIONS

Chiu et al., GABA Transporter Deficiency Causes Tremor, Ataxia, Nervousness, and Increased GABA-Induced Tonic Conductance in Cerebellum. The Journal of Neuroscience, Mar. 23, 2005 • 25(12):3234-3245.*

(Continued)

*Primary Examiner* — Gregory S Emch
*Assistant Examiner* — Aurora M Fontainhas
(74) *Attorney, Agent, or Firm* — Goldilocks ZONE IP LAW

(57) ABSTRACT

A GABA (gamma-aminobutyric acid) release-inhibiting agent in the cerebellum and a composition for treating pathological symptoms caused by over-release of GABA in the cerebellum, each comprising a Bestrophin 1 (Best1) channel inhibitor as an active ingredient; a GABA release-promoting agent in the cerebellum and a composition for treating pathological symptoms caused by the deficit of GABA in the cerebellum, each comprising a Best1 channel activator as an active ingredient; and a method for screening a GABA release-regulating agent in the cerebellum, which uses Best1 channel as target, are provided.

3 Claims, 23 Drawing Sheets
(23 of 23 Drawing Sheet(s) Filed in Color)

(51) Int. Cl.
*G01R 27/28* (2006.01)
*A61K 31/00* (2006.01)
*A61K 31/185* (2006.01)
*A61K 31/196* (2006.01)
*A61K 31/455* (2006.01)
*A61K 31/7105* (2006.01)
*A61K 31/713* (2006.01)
*A61K 38/04* (2006.01)
*A61K 38/08* (2006.01)
*G01N 33/94* (2006.01)

(56) References Cited

OTHER PUBLICATIONS

Minchin et al., Release of [3H]Gamma-Aminobutyric Acid From Glial Cells in Rat Dorsal Root Ganglia. Journal of Neurochemistry, 1974. vol. 23. pp. 533-540.*
Angulo et al., GABA, a forgotten gliotransmitter. Progress in Neurobiology 86 (2008) 297-303.*
Gallo et al., GABA Release Triggered by the Activation of Neuron-Like Non-NMDA Receptors in Cultured Type 2 Astrocytes is Carrier-Mediated GLIA 4: 245-255 (1991).*
Kate E. O'Driscoll, et al., "Functional properties of murine bestrophin 1 channel", Biochemical and Biophysical Research Communications, Jul. 10, 2009. vol. 384, No. 4, pp. 476-481, ISSN 0006-291X.
Luca Raiteri, et al., "Activation of gamma-Aminobutyric Acid GAT-1 Transporters on Glutamatergic Terminals of Mouse Spinal Cord Mediates Glutamate Release Through Anion Channels and by Transporter Reversal", Journal of Neuroscience Research, 2005, vol. 80, pp. 424-433, ISSN 1097-4547.
Vladimir M. Milenkoviv, et al., "Molecular evolution and functional divergence of the bestrophin protein family", BMC Evolutionary Biology, 2008. vol. 8, articles No. 72, pp. 1-10, ISSN 1471-2148.
Masatoshi Ito, et al., "Gaba-Gated Chloride Ion Influx in Brains of Epileptic El Mice", Neurochemical Research, 1990, vol. 15, No. 9, pp. 933-936, ISSN 0364-3190.
International Search Report for PCT/KR2010/005653 mailed May 23, 2011.
Thomas Kuner et al., "A Genetically Encoded Ratiometric Neurotechnique Indicator for Chloride: Capturing Chloride Transients in Cultured Hippocampal Neurons", Neuron, vol. 27, Sep. 2000, pp. 447-459.
K. Berglund et al., "Imaging Synaptic Inhibition in Transgenic Mice Expressing the Chloride Indicator, Clomeleon", NIH Public Access Author Manuscript, Brain Cell Biology, Dec. 2006, pp. 1-33.
Andrea Ventura et al., "Cre-lox-regulated conditional RNA interference from transgenes", PNAS vol. 101, No. 28, Jul. 2004, pp. 10380-10385.
Zhiqiang Qu et al., "The Anion-Selective Pore of the Bestrophins, a Family of Chloride Channels Associated with Retinal Degeneration", The Journal of Neuroscience, May 2006, pp. 5411-5419.
Young Duk Yang et al., "TMEM16A confers receptor-activated calcium-dependent chloride conductance", Nature, vol. 455, No. 30, Oct. 2008, pp. 1210-1216.
Antonella Caputo et al., "TMEM16A, A Membrane Protein Associated with Calcium-Dependent Chloride Channel Activity", Sciencexpress, Sep. 2008, pp. 1-8.
René Barro Soria et al., "Bestrophin-1 Enables $Ca^{2+}$-actived $Cl^-$ Conductance in Epithelia", The Journal of Biological Chemistry, vol. 284, No. 43, Oct. 2009, pp. 29405-29412.
Tom Dull et al., "A Third-Generation Lentivirus Vector with a Conditional Packaging System", Journal of Virology, Vo. 72, No. 11, Nov. 1998, pp. 8463-8471.
C. Justin Lee et al., "Astrocytic control of synaptic NMDA receptors", J Physial, 2007, pp. 1057-1081.
Neil Collinson et al., "Enhanced Learning and Memory and Altered GABAergic Synaptic Transmission in Mice Lacking the a5 Subunit of the $GABA_A$ Receptor", The Journal of Neuroscience, Jul. 2002, pp. 5572-5580.
H Jacob Hanchar et al., "Alcohol-induced motor impairment caused by increased extrasynaptic $GABA_A$ receptor activity", NIH Public Access Author Manuscript, Natural Neuroscience, Mar. 2005, pp. 1-16.
David J. Rossi et al., "Multiple modes of GABAergic inhibition of rat cerebellar granule cells", J Physial, 2003, pp. 97-110.
Martine Hamann et al., "Tonic and Spillover Inhibition of Granule Cells Control Information Flow through Cerebellar Cortex", Neuron, vol. 33, Feb. 2002, pp. 625-633.
Matthew C. Walker et al., "Regulation of Excitability by Extrasynaptic $GABA_A$ Receptors", pp. 29-48, Results Probl Cell Differ. 2008.

* cited by examiner

Cre-lox regulated pSicoR-shRNA lentivirus system

[FIG. 2b]

B1-shRNA  -Tamoxifen

B1-shRNA  +Tamoxifen

Hypothetical schematic for tonic GABA generation

GABA RELEASE-REGULATING AGENT IN CEREBELLUM

CROSS-REFERENCE TO RELATED APPLICATION

This application claims the benefit under 35 U.S.C. Section 371, of PCT International Application No. PCT/KR2010/005653, filed Aug. 24, 2010, which claimed priority to Korean Application No. 10-2009-0077979, filed Aug. 24, 2009 in the Korean Patent Office, the disclosures of which are hereby incorporated by reference.

FIELD OF THE INVENTION

The present invention relates to a GABA (gamma-aminobutyric acid) release-inhibiting agent in the cerebellum and a composition for treating pathological symptoms caused by over-release of GABA in the cerebellum, each comprising a Bestrophin 1 (Best1) channel inhibitor as an active ingredient; a GABA release-promoting agent in the cerebellum and a composition for treating pathological symptoms caused by the deficit of GABA in the cerebellum, each comprising a Best1 channel activator as an active ingredient; and a method for screening a novel GABA release-regulating agent in the cerebellum, which uses Best1 channel as target.

BACKGROUND OF THE INVENTION

GABA is a major inhibitory neurotransmitter in the central nervous system of mammals.

GABA is known to act through two modes of action; tonic and phasic modes. Although it is well established that the mechanism of phasic release of GABA involves a $Ca^{2+}$ dependent vesicular release, the source and the mechanism of tonic GABA release still remains a subject of much speculation.

The present invention has been completed by identifying a mechanism for tonic GABA release.

SUMMARY OF THE INVENTION

An embodiment provides a cerebellar GABA release-regulating agent, which comprises a Best1 channel regulator as an active ingredient.

In particular, the embodiment provides a cerebellar GABA release-inhibiting agent, which comprises a Best1 channel inhibitor as an active ingredient.

In addition, the embodiment provides a cerebellar GABA release-promoting agent, which comprises a Best1 channel activator as an active ingredient.

Another embodiment provides a method of regulating a GABA release in cerebellum, by regulating a Best1 channel activity.

More specifically, the embodiment provides method of inhibiting a GABA release in cerebellum, by inhibiting a Best1 channel activity.

Alternatively, the embodiment provides a method of promoting a GABA release in cerebellum, by activating a Best1 channel activity.

An embodiment of the present invention provides a use of a Best1 channel regulator as an active ingredient for regulating a GABA release in cerebellum.

In particular, the embodiment provides a use of a Best1 channel inhibitor as an active ingredient for inhibiting a GABA release in cerebellum.

In addition, the embodiment provides a use of a Best1 channel activator as an active ingredient for promoting a GABA release in cerebellum.

Another embodiment of the present invention provides a composition for preventing, improving, alleviating, and/or treating a disease or a symptom caused by over-release or deficit of GABA, the composition comprising a Best1 channel activity regulator as an active ingredient.

In particular, the embodiment provides a composition for preventing, improving, alleviating, and/or treating a disease or a symptom caused by over-release of GABA, the composition comprising a Best1 channel inhibitor as an active ingredient.

In addition, the embodiment provides a composition for preventing, improving, alleviating, and/or treating a disease or a symptom caused by deficit of GABA, the composition comprising a Best1 channel activator as an active ingredient.

Another embodiment of the present invention provides a method of preventing, improving, alleviating, and/or treating a disease or a symptom caused by over-release or deficit of GABA, using a Best1 channel activity regulator as an active ingredient.

In particular, the embodiment provides a method of preventing, improving, alleviating, and/or treating a disease or a symptom caused by over-release of GABA, using a Best1 channel inhibitor as an active ingredient.

In addition, the embodiment provides a method of preventing, improving, alleviating, and/or treating a disease or a symptom caused by deficit of GABA, using a Best1 channel activator as an active ingredient.

Another embodiment of the present invention provides a use of a Best1 channel activity regulator as an active ingredient for preventing, improving, alleviating, and/or treating a disease or a symptom caused by over-release or deficit of GABA.

In particular, an embodiment of the present invention provides a use of a Best 1 channel inhibitor as an active ingredient for preventing, improving, alleviating, and/or treating a disease or a symptom caused by over-release of GABA.

In addition, an embodiment of the present invention provides a use of a Best 1 channel activator as an active ingredient for preventing, improving, alleviating, and/or treating a disease or a symptom caused by deficit of GABA.

Another embodiment of the present invention provides a method for screening a cerebellar GABA release-regulating agent by contacting a candidate to a cerebellar sample and determining the extent of Best 1 channel activation thereafter.

DETAILED DESCRIPTION OF THE INVENTION

The present inventors found that tonic GABAergic inhibition is due to a release of GABA from the cerebellar glial cells via an anion Bestrophin 1 (Best 1) channel. The use of a two-cell sniffer patch technique has confirmed that Best1 channel allows a direct permeation of GABA. Secondly, by employing cell-type specific gene slicing technique and latest optogenetic tool as well as conventional electrophysiolologigal approach to detect tonic GABA release in adult mice, the present inventors identified that glial cells contain GABA which can be released through Best1 channel and that the release is inhibited by various anion channel inhibitors. The GABA release was found to significantly decrease by a knock-down of targeted gene after lentiviral Best1-shRNAs were injected into the cerebellar region.

Finally, by combining the cre-lox regulated shRNA system with a hGFAP-CreERT2 transgenic mouse, the present inventors confirmed that attenuation of tonic GABA current due to gene silencing is fully rescued, which indicates that GABA release from glial cells is responsible for ambient GABA. These findings unprecedently conceptualize the role of glial cells and a non-vesicular channel-mediated release mechanism in releasing GABA and highlight the importance of glial integration of neuronal processing.

Since the first observation of tonic GABA current in dentate gyrus granule cells, tonic inhibition has been reported to be distributed differentially throughout the central nervous system including cerebellum, hippocampus, thalamus, cortex, brainstem, and etc. Tonic inhibition dominates over phasic inhibition in controlling the general tone of excitability and carries an important role in information processing of neuronal outputs. The diverse functional roles of tonic inhibition have been implicated in epilepsy, sleep, memory and cognition (Walker and Semyanov, 2008). In the cerebellum, granule cells that provide major excitatory input to Purkinje cells are highly restrained by continuing tonic GABA inhibition, which is mediated by the extrasynaptic, high-affinity subunit-containing $GABA_A$ receptors (Hamann et al., 2002; Rossi et al., 2003). Tonic GABA inhibition in the cerebellum has been reported to be a critical target for low dose alcohol intoxication that impairs motor behavior (Hanchar et al., 2005). However, its functional significance has been explored only in a limited number of studies, partly due to the lack of understanding of the release mechanism.

Cerebellar granule cells form a unique configuration, called type II glomerulus, and allows accumulation of ambient extracellular GABA along with the glutamatergic mossy fiber, the axons of Golgi cell, the granule cell dendrites, and glial sheaths; the glomerulus is completely enclosed with lamella glial sheaths that retain released GABA. Bergmann glial cells, another unique type of astrocyte in the cerebellum, are located proximal to the Purkinje cells (FIG. 1a) and play an important developmental role of providing a scaffold for postnatal granular cell migration and Purkinje cell dendrite maturation. In adults, Bergmann glial cells remain to be a close anatomical and functional partner to Purkinje cells by tightly enwrapping both its somata and synapses in a glial sheath that contains GABAergic synaptic termination from Basket cells and excitatory synaptic terminations from granule cells.

GABA is thought to be synthesized, contained, and released exclusively by neurons in adult brains, but some reports suggest that astrocytes in brainstem and cerebellum contain GABA. In order to determine the presence of GABA in glial cells of adult cerebellum, immunohistochemistry for GABA was performed in GFAP-GFP transgenic mice, in which the somas and the fine processes of GFAP positive astrocytes were labelled with GFP. The immunohistochemistry showed a strong immunoreactivity for antibody against GABA in the somas and the processes of all the GFP-positive Bergmann glial cells as well as in the lamella astrocytes in the granule cell layer (See FIG. 5a and b). Notably, the intensity of glial GABA immunoreactivity was in equal or greater magnitude compared to the neighboring neurons. These results provide a potential support for glial release of GABA.

Previous studies have reported that the tonic activation of $GABA_A$ receptors in cerebellar granule cells of adult rats results from an action-potential-independent, non-vesicular release of GABA. These findings are in line with the idea that the source of ambient GABA may possibly be located in glia. Moreover, in a cell line derived from type-2 astrocytes, the activation of purinergic receptor $P2X_7$ was found to induce the release of $[^3H]$-GABA, which was unexpectedly sensitive to inhibitors of volume-regulated anion channels or $HCO_3^-$/ $Cl^-$ exchangers such as DIDS(4,4'-diisothiocyanato stilbene-2,2'-disulfonic acid) and SITS (4-acetamido-4'-isothiocyanostilbene-2,2'-disulphonic acid). In this context, the present inventors subsequently searched for an anion channel that can serve as a molecular target for GABA release.

Based on the overlapping unique feature of Best1 among anion channels, Best1 was selected to be the candidate anion channel. Human bestrophin-1 (hBest1), among Bestrophins, was cloned to identify a mutation in autosomal dominant Best vitelliform macular dystrophy. It was proven that hBest1 constitutes $Cl^-$ channel that is activated by $Ca^{2+}$ as well as volume change and is readily blocked by Niflumic acid (NFA), NPPB (5-nitro-2(3-phenylpropylamino)-benzoic acid), and DIDS (4,4'-diisothiocyanatostilbene-2,2'-disulfonic acid). In addition to showing much higher permeability to larger anions such as SCN— than Cl—, hBest1 displays a significant permeability ratio for HCO3— compared to Cl— ($P_{HCO3}/P_{Cl}$=0.44).

On the basis of the finding that GABA release is carried out through Best1 channel in the cerebellar glial cells, a disease or a symptom caused by over-release or deficit of GABA can be prevented, mitigated, and treated by the regulation of Bestrophin 1 channel.

Accordingly, an embodiment according to the present invention provides a GABA release-regulating agent, which comprises a Best1 channel activity-regulator as an active ingredient; a method of regulating a GABA release in cerebellum, by regulating a Best1 channel activity; and a use of a Best1 channel regulator as an active ingredient for regulating a GABA release in cerebellum.

Specifically, an embodiment according to the present invention provides a GABA release-inhibitor, which comprises a Best1 channel-inhibitor as an active ingredient; method of inhibiting a GABA release in cerebellum, by inhibiting a Best1 channel activity; and a use of a Best1 channel inhibitor as an active ingredient for inhibiting a GABA release in cerebellum. Alternatively, an embodiment according to the present invention provides a GABA release-promoter, which comprises a Best1 channel-activator as an active ingredient; a method of promoting a GABA release in cerebellum, by activating a Best1 channel activity; and a use of a Best1 channel activator as an active ingredient for promoting a GABA release in cerebellum.

Another embodiment according to the present invention provides a composition for preventing, mitigating, and/or treating a disease or a symptom caused by over-release or deficit of GABA, which comprises a Best1 channel activity-regulator as an active ingredient; a method of preventing, improving, alleviating, and/or treating a disease or a symptom caused by over-release or deficit of GABA, using a Best1 channel activity regulator as an active ingredient; and a use of a Best1 channel activity regulator as an active ingredient for preventing, improving, alleviating, and/or treating a disease or a symptom caused by over-release or deficit of GABA.

Specifically, an embodiment according to the present invention provides a composition for preventing, mitigating, and/or treating a disease or a symptom caused by over-release of GABA, which comprises a Best1 channel-inhibitor as an active ingredient; a method of preventing, improving, alleviating, and/or treating a disease or a symptom caused by over-release of GABA, using a Best1 channel inhibitor as an active ingredient; and a use of a Best1 channel inhibitor as an active ingredient for preventing, improving, alleviating, and/or treating a disease or a symptom caused by over-release of GABA. Alternatively, an embodiment according to the present invention provides a composition for preventing, mitigating, and/or treating a disease or a symptom caused by deficit of GABA, which comprises a Best1 channel-activator as an active ingredient; a method of preventing, improving, alleviating, and/or treating a disease or a symptom caused by deficit of GABA, using a Best1 channel activator as an active ingredient; and a use of a Best1 channel activator as an active ingredient for preventing, improving, alleviating, and/or treating a disease or a symptom caused by deficit of GABA.

Said Bestrophin 1, a type of chloride ion channels, is used as a representative example to show that chloride ion channels allow permeation of GABA. Bestrophin 1 genes can be derived from mammals, preferably from rodents or primates, and can be, for instance but not limited thereto, mouse Bestrophin 1 (mBest1) gene (NM_011913, SEQ ID No. 1) or human Bestrophin 1 (hBest1) gene (NM_004183, SEQ ID No. 2).

Said Best1 channel inhibitor may comprise any substance having an inhibiting activity against the expression of Best1 channel or interfering with and/or blocking, directly or indirectly, the activity of Best1. For instance, the Best1 channel inhibitor can be one or more selected from the group consisting of anion channel blockers and antisense RNAs or shRNAs for Best1 channel-coding nucleotide sequences, without being limited thereto.

Said anion channel blockers can be one or more selected from the group consisting of niflumic acid, flumenamic acid, NPPB (5-nitro-2(3-phenylpropylamino)-benzoic acid), and DIDS (4,4'-diisothiocyanatostilbene-2,2'-disulfonic acid), without being limited thereto. Said antisense RNA can be an antisense RNA for the nucleotide sequence of SEQ ID NO 1 or 2. In addition, said shRNA, indicated by cDNA sequence, can be one or more selected from the group consisting of SEQ ID NOs 3, 4, and 7, without being limited thereto.

(SEQ ID NO: 3)
5'-GATCCCCTTGCCAACTTGTCAATGAATTCAAGAGATTCATTGAC

AAGTTGGCAATTTTTA-3', (SEQ ID NO: 4)
3'-GGGAACGGTTGAACAGTTACTTAAGTTCTCTAAGTAACTGTTCA

ACCGTTAAAAATTCGA-5', (SEQ ID NO: 7)
5'-CGCTGCAGTTGCCAACTTGTCAATGAATTCAAGAGATTCATTGA

CAAGTTGGCAATTTTTGATATCTAGACA-3'.

When GABA release in the cerebellar glial cells is suppressed by inhibiting the activation of Best1 channel, neural GABAergic inhibition, such as tonic inhibition, can be mitigated with the effect of preventing, mitigating, and/or treating a disease or a symptom caused by over-release of GABA. A list of diseases or symptoms caused by over-release of GABA can include epilepsy, sleeping difficulties, memory difficulties, sensory difficulties, cognitive difficulties, motor difficulties, learning difficulties, alcohol addiction, such as low dose alcohol intoxication, and ataxia, without being limited thereto.

Therefore, a composition for preventing, mitigating, and/or treating a disease or a symptom caused by deficit of GABA, which comprises a Best1 channel-activator as an active ingredient, can have an effect of prevention, mitigation and/or treatment for one or more diseases or symptoms selected from the group consisting of epilepsy, sleeping difficulties, memory difficulties, sensory difficulties, cognitive difficulties, motor difficulties, learning difficulties, alcohol addiction, such as low dose alcohol intoxication, and ataxia.

In another aspect of the present invention, an Best1 channel activator according to the present invention facilitates the release of GABA in the cerebellum and is able to increase neural GABAergic inhibition, such as tonic GABAergic inhibition, mitigating the excessive neural excitements caused by over-release of excitatory neurotransmitters. Such Best1 channel activator according to the present invention can be any material or substance having the effect of activating Best1 channel, directly or indirectly. For example, the Best1 channel activator can be an agonist of G-protein coupled receptor (GPCR), such as peptide TFLLR and Bradykinin, without being limited thereto. Such Best1 channel activation promotes the release of GABA. And the neural inhibition by the released GABA, e.g., tonic GABAergic inhibition, can have an effect of preventing, mitigation, and/or treating pathological symptoms caused by excessive neural excitement, for example, memory related diseases (Alzheimer, memory loss with aging, and etc.), seizures, excitotoxicity, ischemia, cerebral apoplexy, cerebral hemorrhage, epilepsy, brain injuries, and hypoxia. Accordingly, a composition for preventing, mitigating, and/or treating a disease or symptoms cased by GABA deficits, which comprises Bestrophin 1 channer activity-inhibitor as an active ingredient, can have an effect of prevention, mitigation, and/or treatment on one or more kinds selected from the group consisting of memory-related diseases (Alzheimer, memory loss with aging, and etc.), seizures, excitotoxicity, ischemia, cerebral apoplexy, cerebral hemorrhage, epilepsy, brain injuries, hypoxia.

According to the present invention, the GABA release-regulating agent and the composition, the method, and/or the use for preventing, mitigating, and/or treating diseases and/or symptoms caused by over-release or deficit of GABA may be one to be administered to mammals, preferably to humans.

Another aspect of the present invention relates to a method for screening a novel cerebellar GABA release-regulating agent, in which the screening is performed using Best1 channel as a target in the cerebellum, more specifically, Best1 channel in the cerebellar glial cells.

The above screening method can comprise the steps of:
preparing a cerebellar sample;
allowing the contact of a candidate to the cerebellar sample; and
observing the activation of Best1 channel in the cerebellar sample.

In the screening method, the candidate is determined to be a GABA release-promoting agent when the Best1 channel is found to be activated, whereas the candidate is determined to be a GABA release-inhibiting agent when the Best1 channel is found to be inactivated.

Determination of whether the Best1 channel is activated can be performed using any method known in the technology field to which the present invention belongs. For example, the determination can be made in a manner in which other channels and receptors are made inactive except the Best1 channel in the cerebellar glial cells, and then inward current changes are measured. Increased inward currents after the treatment of a candidate suggest that the Best1 channel is activated, whereas decreased inward currents after the treatment of a candidate suggest that the Best1 channel is inactivated. Inactivation of other channels and receptors and determination of inward currents are of technology widely known in the technology field to which the present invention belongs, and those skilled in the art can perform easily. For instance, determination of inward currents can be carried out using sniffer patch technique (see 'Lee, C. J. et al. Astrocytic control of synaptic NMDA receptors. *J Physiol* 581, 1057-81 (2007)', which is incorporated hereto as a reference).

In the screening method according to the present invention, the cerebellar sample can be obtained from mammals, preferably from rodents or primates.

By identifying the mechanism of tonic GABA release via a Best1 channel in the cerebellum, it is expected to more effectively regulate the GABA release as well as GABA-related pathological symptoms.

BRIEF DESCRIPTION OF THE DRAWINGS

The patent or application file contains at least one drawing executed in color. Copies of this patent or patent application publication with color drawing(s) will be provided by the Office upon request and payment of the necessary fee.

FIGS. 1a-1d represent GABA containing cerebellar glial cells which express bestrophin 1 channel that can release GABA by direct permeation, wherein FIG. 1a shows confocal images of immunohistochemistry with antibodies against GFP, Best1, and GABA in GFAP-GFP transgenic mouse cerebellum;

FIG. 1b is schematic of two-cell sniffer patch; and

FIG. 1c shows the result of the extent of permeation.

FIG. 1d shows the degree of GABA release activity under the stated conditions.

FIG. 2b shows the timeline of experiment with B6 or GFAP-GFP mice.

FIGS. 3a-3i show that tonic GABA current is inhibited by anion channel blocker and decreased by gene silencing of bestrophin channel, wherein FIG. 3a shows cerebellar slice of CLM1 clomeleon mouse showing bright fluorescent granular cell bodies in granule cell layer and parallel fibers located in molecular layer, separated by translucent Purkinje cell layer (black arrows);

FIG. 3b shows ratiometric imaging of clomeleon revealing the time course of $[Cl^-]_i$ change;

FIG. 3c demonstrates a graph that shows the correlation between $[Cl^-]_i$ change by NPPB and $[Cl^-]_i$ change by SR;

FIG. 3d is colmeleon imaging from mouse injected with scrambled-shRNA lentivirus;

FIG. 3e is clomeleon imaging from mouse injected with B1-shRNA;

FIG. 3f is summary of clomeleon imaging in each virus type and each layer;

FIG. 3g shows raw traces of tonic GABA current from granular cell in cerebellar slice (holding potential at −60 mV) of 8 wks B6 mice;

FIG. 3h is summary figure of GABAzine-sensitive current from naïve, scrambled, and B1-shRNA injected mice; and FIG. 3i is summary figure for NPPB sensitive current.

FIGS. 4a-4f show that glia specific rescue of Best1 channel restores tonic GABA current, wherein FIG. 4a is the timeline of experiment for hGFAP-CreERT mice;

FIG. 4b shows a typical glial-specific rescue mechanism;

FIG. 4c shows the whole-cell patch clamp recording from granular cells;

FIG. 4d shows the GABAzine-sensitive currents in case of naive, shRNA and shRNA+Tamoxifen;

FIG. 4e shows the NPPB-sensitive currents in case of naive, shRNA and shRNA+Tamoxifen; and FIG. 4f is a proposed model of tonic GABA release in cerebellum.

FIG. 5 shows that glial cells strongly express mBest1 and GABA in adult mice cerebellum, wherein FIG. 5a illustrates concocal images of immunocytochemistry for GABA, Best1 and GFAP-GFP in mice cerebellum;

FIG. 5b shows higher magnification of GABA and GFAP-GFP staining in cerebellum; and FIG. 5c shows higher magnification (×60) of Best1 and GFAP staining.

FIGS. 6a-6g shows that tonic GABA release in the cerebellar granular cell layer is Ca2+ dependent, non-vesicular, and inhibited by anion channel blockers, wherein FIG. 6a shows bright field images of granular and molecular cell layers (upper panel; ×40, lower panel; ×600) which are used to obtain the results in 6a-6g;

FIGS. 6b-6e each shows tonic GABA current recordings with the application of 100 μM Niflumic acid (NFA), incubation with 150 μM of BAPTA-AM, incubation with 0.5 μM concanamycin A, and application of 30 μM NPPB, respectively;

FIG. 6f shows summarized results of GABAzine sensitive current with no treatment, concanamycin A treatment and BAPTA-AM treatment; and FIG. 6g is the block percentage of tonic current by $Ca^{2+}$ sensitive Cl⁻ channel blockers.

FIGS. 7a-7d indicate that NPPB does not directly affect GABA receptors, wherein

FIGS. 7a and 7b show the results when GABAc expressing HEK293 cells were patch clamped and challenged with 100 μM GABA in the absence and presence of 100 μM NFA and 100 μM NPPB; and FIGS. 7c and 7d show the application of NPPB which does not affect GABA receptors in cerebellar granule cells, and the magnitudes of GABA induced current with the NPPB application (2 and 5 min) compared to the baseline;

EXAMPLES

Figures 1A, 1B:
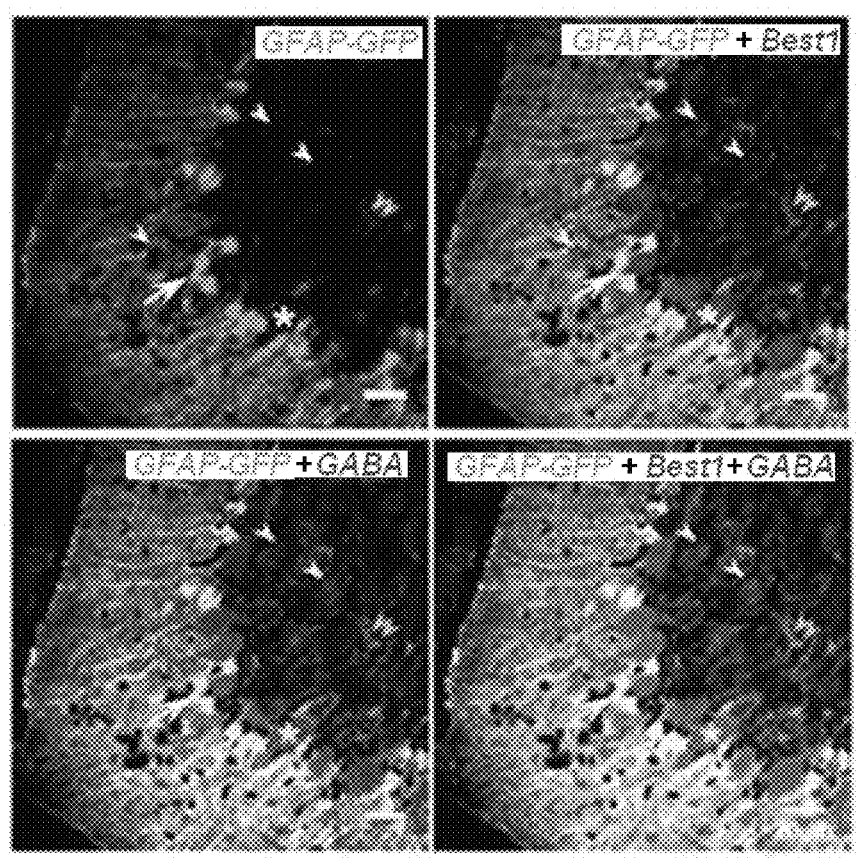

The present invention is further explained in more detail with reference to the following examples. These examples, however, should not be interpreted as limiting the scope of the present invention in any manner.

Example 1

Gene Cloning and shRNA Virus Vector Construction 1.1: Cloning of Best1

For the cloning of full-length mouse bestrophin 1 (mBest1) cDNA, total RNA obtained from cultured astrocytes of P0~P3 postnatal mice (C57BL/6, cerebral cortex; SPF room, Center for Neural Science, KIST, Seoul, Korea) or testis of adult male mice (C57BL/6) was purified, and cDNA was synthesized using Super Script III reverse transcriptase (Invitrogen). Using 21 base primer pair (mBest1-F: 5'-aggacgatgatgattttgag-3' (SEQ ID NO: 5), mBest1-R: 5'-ctttctggtttttctggttg-3' (SEQ ID NO: 6)) spanning the open-reading frame based on NCBI database cDNA [GenBank accession numbers NM_011913 XM_129203], PCR was performed to acquire full-length ORF of mBest1. Resulting PCR products were cloned into a pGEM-T easy vector (Promega) and the sequence was verified.

1.2: Plasmid Construction of Best1 and Expression

In order to express mBest1 in mammalian cell, mBest1 full-length fragment from pGEM-T easy plasmid (6.65 kb, Promega) was subcloned into pcDNA 3.1 (Invitrogen) by using HindIII(NEB) and NotI (NEB) sites or pIRES2-dsRED (Invitrogen) by using XbaI (NEB) and XmaI (NEB) sites. The pcDNA3.1-mBest1 plasmid was transfected into HEK293T cells (ATCC) with ⅒ quantity of pEGFP-N1 plasmid (Invitrogen) using effectene transfection reagent (Qiagen) to detect mBest1-expressing cells. Cells with green fluorescence were selected when both pcDNA3.1-mBest1 and pEGFP-N1 were transfected, whereas cells with red fluorescence were selected when pIRES2-dsRED vector plasmid was transfected. One day after transfection, cells were replated onto glass coverslips for electrophysiological recording. The transfected cells were used for patch clamp experiments within 24-36 hrs.

1.3: Best1 shRNA and Lentivirus Production

For plasmid-based shRNA expression, the following complementary oligonucleotides were annealed and inserted into the HindIII/BglII sites of pSUPER-GFP vector (Oligo Engine):

```
                                              (SEQ ID NO: 3)
5'-GATCCCCTTGCCAACTTGTCAATGAATTCAAGAGATTCATTGAC

AAGTTGGCAATTTTTA-3';

(SEQ ID NO: 4)
3'-GGGAACGGTTGAACAGTTACTTAAGTTCTCTAAGTAACTGTTCA

ACCGTTAAAAATTCGA-5',
```

(The nucleotide sequence corresponding to of mBest1 (563-582) is included. The remaining sequences are included for the purpose of hairpin shape and cloning.

For lentivirus-based shRNA expression, lentiviral vector containing mBest1 gene was constructed by inserting synthetic double-strand oligonucleotides 5'-CGCTGCAGTTGCCAACTTGTCAATGAATTCAAGAGATTCATTGACAAGTTGG CAATTTTTGATATCTAGACA-3' (SEQ ID NO: 7) into pstI-XbaI restriction enzyme sites of shLenti2.4 CMV lentiviral vector (Macrogen) and verified by sequencing. Scrambled oligonucleotides-containing-shLenti construct (used as a control for target shRNA that degrades mRNA by recognizing particular sequences and composed of sequences that do not degrade cellar mRNA, Macrogen) was used as control. The production of lentivirus was performed by Macrogen Inc. (see Dull, T. et al., A third-generation lentivirus vector with a conditional packaging system. J Virol 72, 8463-71 (1998), which is incorporated hereto as a reference).

In the following Example 2, Best1 targeting shRNA lentiviral inserted with SEQ ID NO: 7 was used.

Example 2

Immunochemistry: Verification of Co-Expression of GABA and Best1 in Glial Cells

Figure 5:
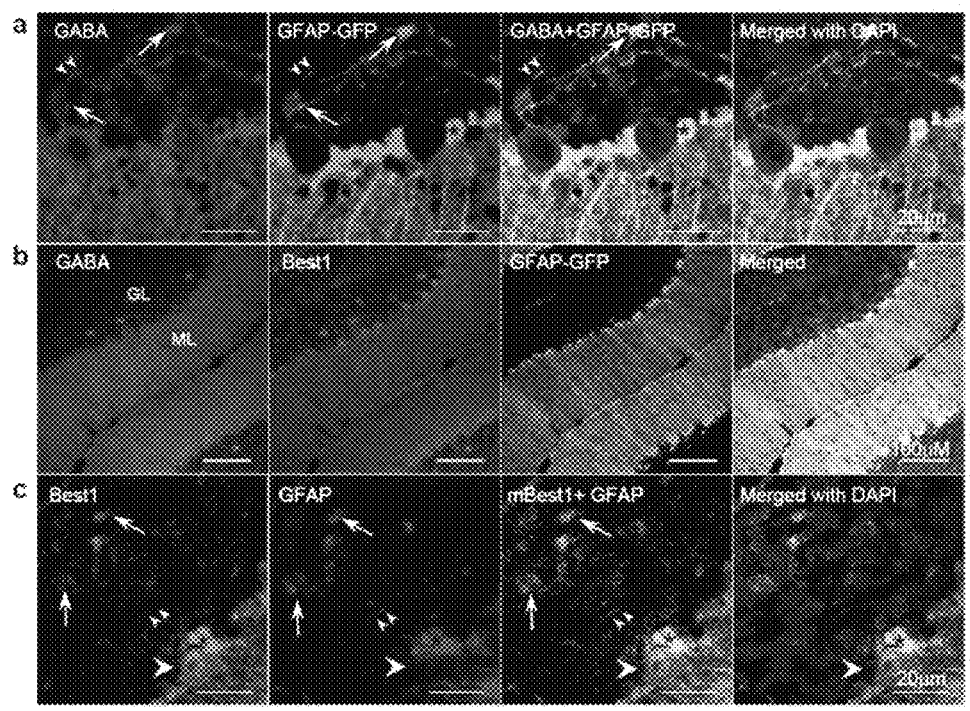

In order to verify the expression of Best1 in the cerebellum, immunochemistry was performed by using antibodies raised against Best1 and GABA in a GFAP-GFP transgenic mouse (FIG. 5c).

Adult GFAP-GFP mice (SPF room, Center for Neural Science, KIST, Seoul, Korea) or lentivirus (Best1 targeting shRNA lentivirus in Example 4) injected GFAP-GFP mice were fixed with 4% paraformaldehyde. 30 µm sagittal cryostat sections of cerebellum were rinsed in PBS 3 times and incubated for 1 hr in blocking solution (0.3% Triton-X, 2% normal serum in 0.1 M PBS, sigma). After incubating overnight in blocking solution containing the mixture of rabbit anti-mouse bestrophin antibody (1:100, (Soria et al, 2006)) and chicken anti-GFP antibody (1:1,000, abcam) and guinea pig anti GABA antibody (1:1,000, Chemicon) at 4° C. on shaker, the cryostat sections were washed 3 times in PBS, and then in Alexa 488, 555 and 647 conjugated with corresponding secondary antibodies. The resulting products were washed 3 times in PBS and mounted with fluorescent mounting medium (Dako, S3023). Confocal series of fluorescence images were obtained using FV1000 confocal microscope (Olympus). The images were processed using Olympus FLUOVIEW software ver.1.7.

FIG. 1a represents confocal images of immunohistochemistry with antibodies against GFP, Best1, and GABA in GFAP-GFP transgenic mouse cerebellum.

FIG. 1a (upper left) shows a confocal image of GFAP-GFP staining (green) that labels Bergmann glial cells (arrow) and lamella astrocytes (pale blue arrowheads). Purkinje cell (star) is devoid of GFAP-GFP staining. FIG. 1a (upper right) is a confocal image depicting both GFAP-GFP staining and Best1 staining (red). Best1, expressed in Purkinje cells (star) and other neurons (arrowheads), is also highly expressed in glial cells (pale blue arrowheads) in granular layer and Bergmann glial cells (arrow) in molecular layer. FIG. 1 (*lower* left) shows merged GFAP-GFP and GABA staining (magenta). In addition to GABAergic neurons, GABA is strongly coexpressed with GFAP-GFP in Bergmann glial cells (arrow) and lamella astrocytes (pale blue arrowheads). FIG. 1a (lower right) represents merged images of GFAP-GFP, mBest1 and GABA. According to FIG. 1a, Best1 immunoreactivity intensity is observed in Bergmann glial cells (arrow), lamella astroctyes (pale blue arrowheads), and GABAergic neuron, but not in granular cells.

FIG. 5a-c is a picture showing a strong expression of mBest1 and GABA in glial cells of adult mouse cerebellum.

FIG. 5a is an immunohistochemistry confocal images for GABA, Best1 and GFAP-GFP in mouse cerebellum. Immunohistochemical studies show that GABA (First Panel) and Best1 (Second Panel) are intensely expressed in molecular layer than granular cell layer. The third panel indicates that Bergmann glial process occupy the most of region in molecular layer. The last panel shows the merged confocal image of GABA, Best1 and GFAP-GFP.

FIG. 5b shows a higher magnification image of GABA and GFAP-GFP staining in cerebellum. GABA is heavily stained with Perkinje cells and GABAergic interneurons in molecular layer. However, surprisingly, Bergmann glical cells (star) also express strong GABA immunoreactivity in their soma and processes (small black arrowheads). Glial cells in granular layer (arrow) are stained with GABA with lighter intensity, and their processes are also stained with GABA (small white arrows).

FIG. 5c shows a higher magnification (×60) image of Best1 and GFAP staining. mBest1 is highly expressed in glial cells (arrows) of granular layer and Bergmann glial cells (star) of molecular layer. Big arrowhead indicates Perkinje cells that express mBest1 but devoid of GFAP staining. Small arrowheads indicate astrocytic process in granular layer. Astrocytic processes also express mBest1. The right most panel shows granular cells heavily stained with DAPI but no mBest1 and GFAP immunoreativity were observed. GABA GFAP-GFP GABA+GFAP-GFP Merged with DAPIed As illustrated in FIG. 5a-c, Bergmann glial cell processes, that are located along Purkinje cell body and dendritic trees in molecular layer where parallel fibers and climbing fibers are close to and interact with each other, co-expressed Best1 and GABA. These results raise an intriguing possibility that the Best1 channel could serve as a molecular target for glial release of GABA in cerebellum.

Example 3

Two-Cell Sniffer Patch—Verification of Best1 Channel Mediated GABA Release

For Best1 channel to mediate release of GABA, it has to permeate GABA upon channel opening. To test for GABA permeability of Best1 channel, a two-cell sniffer patch technique was developed to directly measure GABA release via Best1 channel in sensor HEK293T cells that express GABAc, and via other channels that are expressed in source HEK293T cells (FIG. 1b).

pIRES-Best1-dsRED plasmid (obtained by cloning Best1 using pIRES-dsRED (Invitrogen)) and GABAc with GFP (obtained by cloning GABAc using pcDNA3.1 (Invitrogen)) were transfected into HEK 293T cells (ATCC) using Effectene transfection reagent (Qiagen). 18~24 hrs after transfection, cells were replated together onto glass coverslips for electrophysiological recording and those cells were used for patch clamp experiments within 24~36 hrs. For recording, one of adjacent two cells consisting of a dsRED stained cell (Red) transfected with pIRES-Best1-dsRED and a GFP stained cell (Green) transfected with GABAc with were selectively patched.

The patch pipette internal solution containing 3 or 140 mM GABA which serves as the source of GABA release, and free $Ca^{2+}$ (~4.5 μM) at a concentration within physiological range (micromole) which activates Best1 channel, was used. FIG. 1b is a schematic diagram of two-cell sniffer patch illustrating HEK cells which express Best1 (coexpressing dsRed) or GABAc (co-expressing GFP). The picture at the bottom of FIG. 1b depicts intracellular pipetting of 3 or 145 mM GABA and 0 or 4.5 μM $Ca^{2+}$ into the source. The bright field and fluorescence images of source and sensor cells are also shown at the bottom of FIG. 1b.

For the source of GABA release, the pipette solution containing 3 mM GABA(Tocris) 146 mM CsCl, 5 mM $(Ca^{2+})$-EGTA[ethylene glycol bis(2-aminoethyl-ether)-N,N,N',N'-tetraacetic acid]-NMDG(N-methyl-D-glucamine), 2 mM $MgCl_2$, 10 mM HEPES, 10 mM sucrose, 4 mM Mg-ATP and 0.3 mM $Na_2$-GTP (pH; 7.3) was used. For the sensor, the pipette solution containing 110 mM D-gluconate, 110 mM CsOH, 30 mM CsCl, 2 mM $MgCl_2$, 4 mM NaCl, 5 mM EGTA(ethylene glycol bis(2-aminoethyl-ether)-N,N,N',N'-tetraacetic acid), 4 mM Mg-ATP, and 0.3 mM $Na_2$-GTP (pH; 7.3) was used. For 3 mM GABA Zero $Ca^{2+}$ experiment, 5 mM $(Ca^{2+})$-EGTA-NMDG was replaced by 5 mM EGTA-NMDG. For 140 mM GABA experiment, 3 mM GABA and 146 mM CsCl were replaced by 140 mM GABA. pH was adjusted with CsCl and osmolarity was adjusted to 290 mOsmol.

The internal solution containing 150 mM NaCl, 10 mM HEPES, 3 mM KCl, 2 mM $CaCl_2$, 2 mM $MgCl_2$, and 5.5 mM Glucose was used. If the source channel can permeate GABA, GABAc receptor on neighboring cell bind to released GABA and $Cl^-$ inward current would be elicited. Full activation of GABA current was obtained by bath application of 100 μM GABA and normalized for the purpose of comparison.

GABA release was induced by a break-though of membrane patch that goes into a whole-cell configuration in the source cell and such the released GABA was monitored and detected by a neighboring sensor cell. Full activation of GABA current was obtained by bath application of 100 μM GABA and the percentage of full activation was calculated (FIGS. 1c and 1d).

Figure 1C:
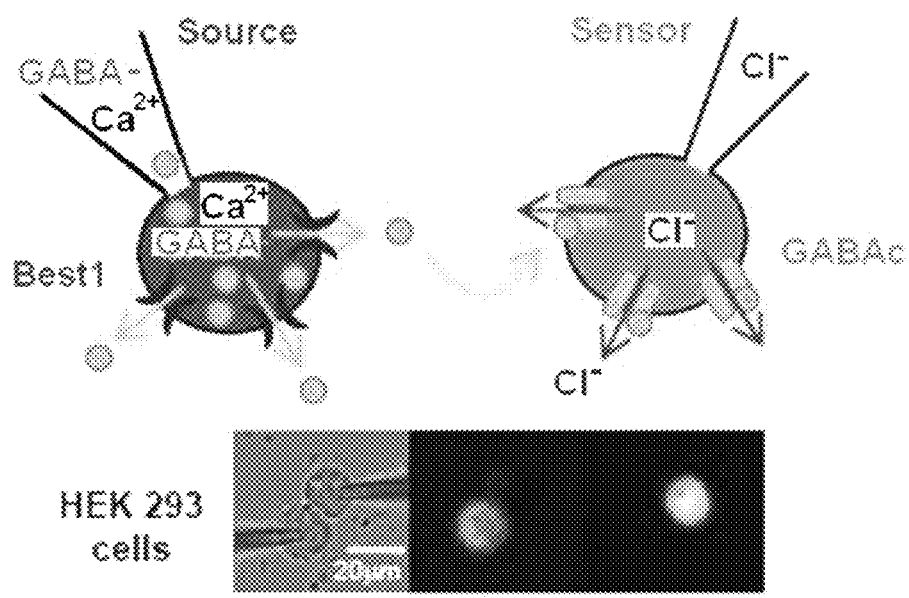

FIG. 1c shows the result of permeation experiment. Permeated GABA is detected in sensor as an inward current (bottom traces). The time period for a membrane breakthrough to go into whole-cell mode is indicated as a black arrowhead on the source trace (top traces). NPPB was used at 100 μM. Best1* (B1*) is a pore mutant Best1-W93C (Qu et al, 2006). The GABA permeability of said mutant was determined by using cells obtained by transfecting said mutant into HEK293t cell (ATCC). ANO1 is the recently characterized TMEM16A Ca2+ activated chloride channel (Yang et al., 2008, Caputo et al., 2008; Dr. Park Lab, Gyeongsang National University, Korea). The GABA permeability of said AN01 was determined by using cells obtained by transfecting said mutant into HEK293t cell (ACTT).

Figure 1D:
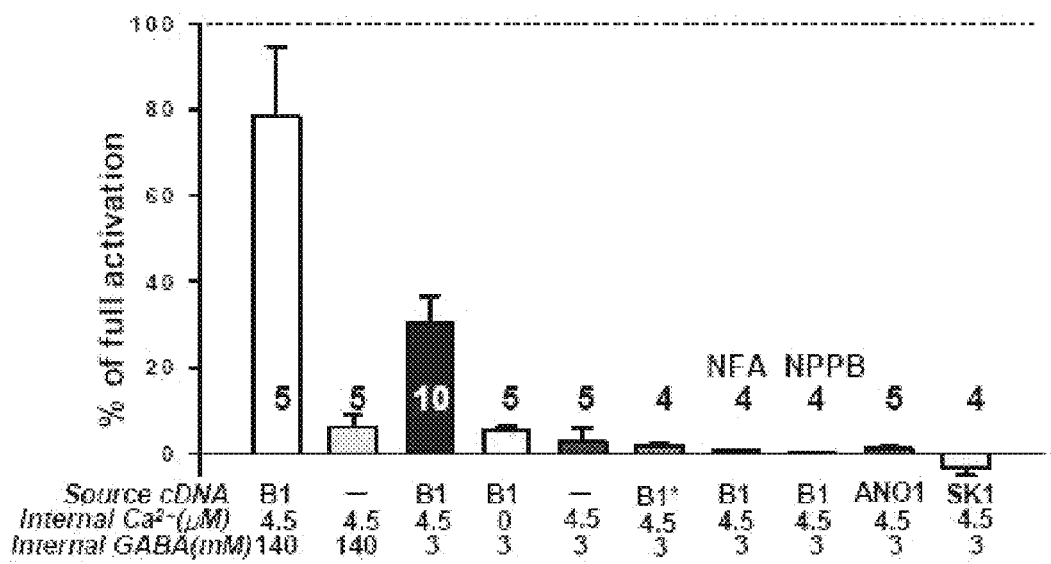

FIG. 1d is a summary of the extent of GABA release in various conditions. GABA release detected as a inward current in sensor cell is normalized to a full activation with 100 μM GABA and then the percentage of full activation was calculated. NPPB and NFA were used at 100 μM. SK1 is small conductance Ca2+ activated K+ channel (Dr. Adelman Lab). The GABA permeability of said SK1 was determined by using cells obtained by transfecting said mutant into HEK293t cell (ACTT). Averages are expressed as mean+SEM (standard error of the mean). Student's t-test was used throughout the experiment (unpaired, 2-tailed).

As illustrated in FIGS. 1b, 1c and 1d, Best1 channel uniquely displayed a significant permeability for GABA, whereas recently characterized Ano1 (or TMEM-16A, Yang et al, 2008, Caputo et al, 2008) or $Ca^{2+}$ activated potassium channel, SK1 did not show any permeability for GABA. The GABA release via Best1 was completely abolished by anion channel blockers, NFA and NPPB and was dependent on intracellular $Ca^{2+}$ and GABA concentration (FIG. 1c,d). In addition, as shown in FIG. 1d, one of the known pore mutants of Best1, Best1-W93C (Qu et al, 2006) did not show any GABA permeability, supporting the idea of GABA permeation occurs through the pore of Best1 channel.

In addition, FIG. 7 shows that the inhibition of GABA release by NFA and NPPB is not obtained by directly affecting the GABAc receptors. In FIGS. 7a and 7b, GABAc expressing HEK293 cells were patch clamped and challenged with 100 μM GABA in the absence or presence of 100 μM NFA and 100 μM NPPB. NFA and NPPB application do not have significant impact on GABA release in the GABAc expressing HEK293 cells.

These results raise a possibility that Best1 channels can mediate GABA release through direct permeation in native cells.

Example 4

Transgenic Mouse Experiment—Verification of Best1 Channel Mediated GABA Release

4.1: Trangenic Mouse Construction

Figure 2A:
FIG. 2a is schematic of Cre-lox regulated pSicoR-shRNA lentivirus construct.
Figure 2A:
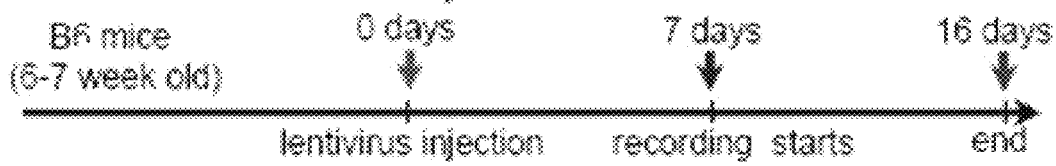

To test whether native Bergmann glial cells express functional Best1 channel that can permeate GABA and further manipulate Best1 channel at the molecular level, a lentivirus carrying a mCherry-tagged small hairpin-forming interference RNA (shRNA), which is under the regulation of Cre-loxP recombination, inducing cell-type specific gene silencing when used in combination with Cre-expressing transgenic mice was constructed (FIG. 2a, Ventura et al., 2004). FIG. 2a is Cre-lox regulated pSicoR-shRNA lentivirus construct (Best1-shRNA cloned with pSicoR vector purchased from ADD Gene). The lentivirus carrying mCherry-tagged shRNA was constructed by attaching mCherry to Cre-lox regulated pSicoR-shRNA lentivirus construct. The two loxP sites are located in the area that includes shRNA under U6 promoter and mCherry under CMV promoter. When Cre recombinase is expressed, it excise out these cassettes, making shRNA inactive.

The Best1-targeting shRNA lentivirus (prepared in Example 1.3) was injected streotactically into cerebellar cortex of 6-7 week old GFAP-GFP mouse (SPF room, Center for Neural Science, KIST, Seoul, Korea) (FIG. 2b). FIG. 2b shows the time line of experiment with B6 (SPF room, Center for Neural Science, KIST, Seoul, Korea) or GFAP-GFP mice. Mice were injected at 6-7 week age. After 7 days from lentivirus injection into cerebellum, immunohistochemistry or whole-cell recordings were performed.

Example 4.2

Immunohistochemical Analysis Using Transgenic Mouse

Figure 2C:
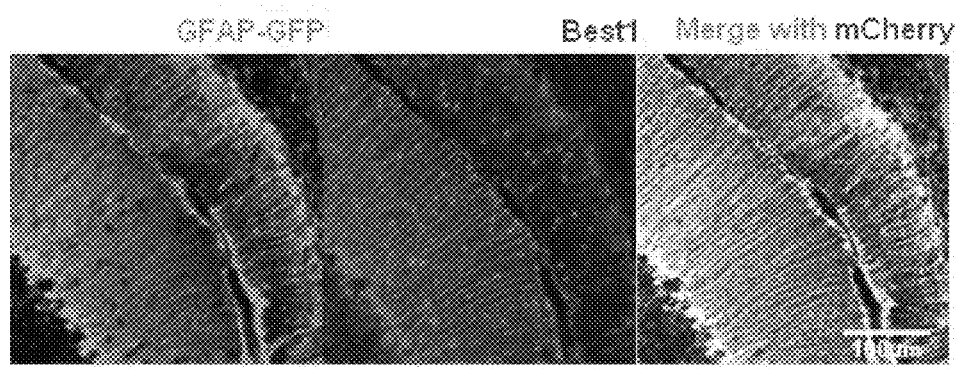
FIG. 2c shows B1-shRNA lentivirus containing GFAP-GFP (green) staining, Best1 (magenta) and mCherry (red).
Figure 2C:
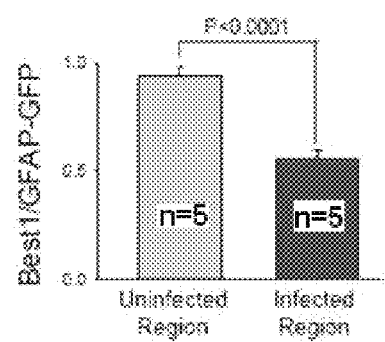
Figure 8A:
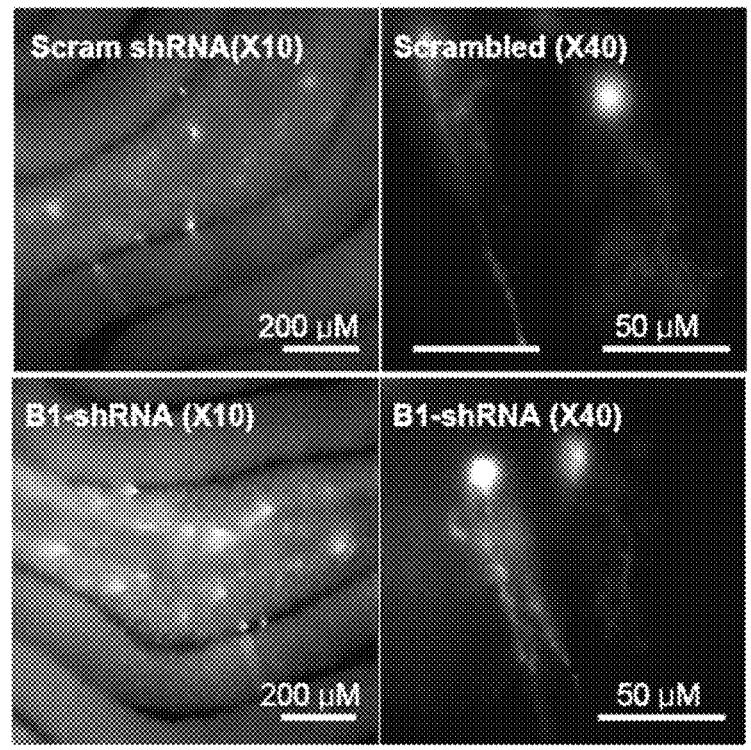
FIG. 8a shows fluorescence images of mCherry signals in shRNA and scrambled RNA injected mice (Scale bars; 200 μm (×10) and 50 μm (×40)).

The cells transfected with the lentivirus were extensively distributed in the molecular layer as well as granular cell layer (FIG. 2c, right and FIG. 8a). FIG. 2c shows B1-shRNA lentivirus carrying GFAP-GFP (green) staining, Best1 (magenta) and mCherry (red). Best1 immunoreactivity is significantly reduced in virus injected area compared to uninfected area. Intensities for GFAP-GFP in both area are relatively similar. Right most, the knockdown efficiency is expressed as Best1 intensity normalized by GFAP-GFP intensity after thresholding with GFAP-GFP. The pixel intensity of Best1 immunoreactivity in infected region decreased dramatically compared to the uninfected regions (FIG. 2c, far right), confirming both the high efficiency of Best1-shRNA and specificity of Best1 antibody.

4.3: Recording of Whole-Cell Patch Clamp Using Transgenic Mouse

4.3.1: Construction of Cerebellum Slice

Brain slices were prepared as described in Rossi et al., 2003. For slice recording, either approximately P28 days old or more than 8 weeks old mice were used. Animals were deeply anesthetized with halothane. After decapitation, the brain was quickly excised from the skull and submerged in ice-cold cutting solution (in mM): 250 Sucrose, 26 $NaHCO_3$, 10 D(+)-Glucose, 4 $MgCl_2$, 3 myo-inositol, 2.5 KCl, 2 Sodium pyruvate, 1.25 $NaH_2PO_4$, 0.5 Ascorbic acid 0.1 $CaCl_2$, 1 Kynurenic acid, pH 7.4. All solutions were gas-treated with 95% $O_2$-5% $CO_2$. After trimming both sides of vermis, several parasagittal slices with 250 μM thicknesses containing cerebellar lobes were cut using a microtome (Leica VT 1000) and transferred to extracellular ACSF solution (in mM); 126 NaCl, 24 $NaHCO_3$, 1 $NaH_2PO_4$, 2.5 KCl, 2.5 $CaCl_2$, 2 $MgCl_2$, 10 D(+)-Glucose, pH 7.4. Slices were incubated for one hour at least at room temperature.

4.3.2: Recording of Whole-Cell Patch

For recording, slices were transferred to an electrophysiological recording chamber (RC-26G, Warner Instruments) which is continuously superfused with ASCF (artificial cerebrospinal fluid, sigma) solution (flow rate; 2 ml/min) and controlled by flower controller (Synaptosoft) and a vacuum pump (Charles Austen, model Capex 8C). Slice chamber was mounted on the stage of an upright microscope (Olympus, Japan) and viewed with an ×60 water immersion objective with differential interference contrast and infrared optics. Cellular morphologies were visually identified by Imaging Workbench 6.0 (INDEC Systems, Inc), camera controller (Hamamatsu, C4742-95), and light microscope controller (Olympus, TH4-200). Fluorescence images were viewed with mercury lamp (Olympus, U-RFL-T). Whole cell voltage-clamp recording was made from granular cell somata or Bergmann glial cells mostly located in 2-5 cerebellar lobules For Bergmann glial cell recording patch pipettes (8-10 MΩ) were constructed from thick-walled borosilicate glass capillaries (SC150E-10, Warner instrument Corp). For 0 GABA comparison experiment, pipette was filled with an internal solution containing (in mM); 146 CsCl, 5 ($Ca^{2+}$)-EGTA-NMDG, 2 $MgCl_2$, 8 HEPES and 10 Sucrose, 4 Mg-ATP, and 0.3 $Na_2$-GTP (pH; 7.3).

For 140 mM GABA experiment, internal solution containing 140 mM GABA, 5 ($Ca^{2+}$)-EGTA-NMDG, 2 mM $MgCl_2$, 10 mM HEPES, 10 mM Sucrose, 4 mM Mg-ATP, and 0.3 mM $Na_2$-GTP (pH; 7.3 with CsOH). Osmolarity was adjusted to 297 and 290 mOsmol was used. Bergmann glial cells were visually identified by GFP fluoscence image. Holding potential for voltage clamping of Bergmann glial cell was −70 mV.

Pipette resistance for granule cells was typically 10-12 MΩ and pipette was filled with an internal solution containing (in mM) 135 CsCl, 4 NaCl, 0.5 $CaCl_2$, 10 HEPES, 5 EGTA, 2 Mg-ATP, 0.5 $Na_2$-GTP, 10 QX-314, pH adjusted to 7.2 with CsOH (278-285 mOsmol) was used (Rossi, et al., 2003). With this internal solution, $E_{cl}$=0 mV with voltage clamp and holding potential of −60 mV, inward current was elicited.

Electrode junction potentials for Bergmann glial cells recording were corrected but junction potential for granular cell recording was not corrected. Junction potentials were +3.5 mV and −9.7 mV in 0 GABA and 140 GABA experiments, respectively.

For puffing experiment, glass electrode (5-6 MΩ) filled with 100 mM was positioned near to the patched granular cell and puffed briefly for 500 ms by Picospritzer III (Parker instrumentation) connected with MiniDigi (Molecular Device).

For Purkinje cell recording, patch pipette (2-3 MΩ) was filled with an internal solution containing (in mM) 140 K-gluconate, 10 KCl, 1 $MgCl_2$, 10 HEPES, 0.02 EGTA, 4 Mg-ATP, 0.4 $Na_2$-GTP pH adjusted to 7.35 with KOH (Osmol: 278-285) was used. The data recorded from the cell with access resistance over 30 MΩ were discarded.

The signals were digitized and sampled at 50 μs intervals with Digidata 1440A (Molecular Devices) and Multiclamp 700B amplifier (Molecular Devices) using pCLAMP 10.2 sofware (Molecular Devices). Off-line analysis was carried out using Clampfit 10.2 (Molecular Devices), Minianalysis (Synaptosoft, USA), SigmaPlot 10.0 (SPSS) and Excel 2003 (Microsoft).

4.3.3: Drug Application

All the drugs and chemicals used in this study were purchased from Sigma-Aldrich if not mentioned otherwise; Lidocaine N-ethyl bromide (QX-314, Sigma), SR95531 hydrobromide (GABAzine, Tocris), concanamycinA (Tocris), BAPTA-AM (1,2-Bis(2-aminophenoxy)ethane-N,N,N', N'-tetraacetic acid tetrakis(acetoxymethyl ester), Tocris), Fluronic® F-127 (invitrogen), Niflumic acid (Sigma), NPPB (5-Nitro-2-(3-phenylpropylamino)benzoic acid, Tocris), DIDS (4,4'-Diisothiocyanatostilbene-2,2'-disulfonic acid disodium salt hydrate, Sigma).

4.4.4: Data analysis and Statistical analysis

Numerical data was presented as means±S.E.M. The significance of data for comparison was assessed by Student's two-tailed unpaired t test and significance level was displayed as * ($p<0.05$),  ($p<0.01$), *($p<0.001$). Data were filtered at 2 kHz, Goldman-Hodgkin-Katz equation was calculated as below and $P_X/P_{Cl^-}$ was calculated.

$$E_{rev}=RT/F \cdot ln\{PCl^-[Cl^-]_i+P_X[X]_i\}/\{PCl^-[Cl^-]_o+Px[X]_o\}$$

4.4.5: Result

Figure 2D:
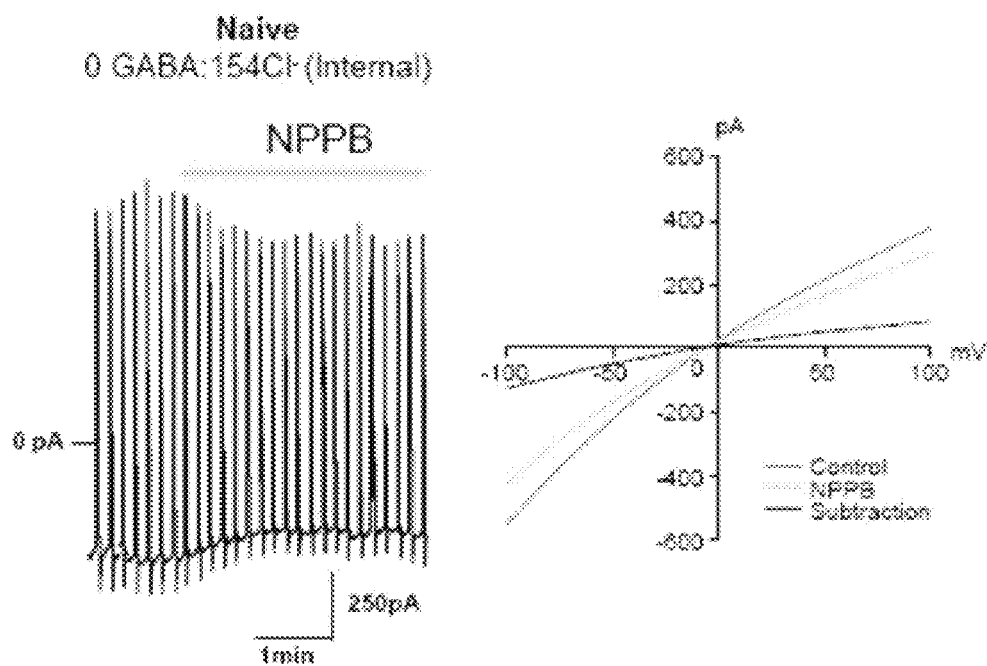
FIG. 2d shows the result of glial cell patch recording using the ramp protocol (Vh=−70 mV).
Figure 2E:
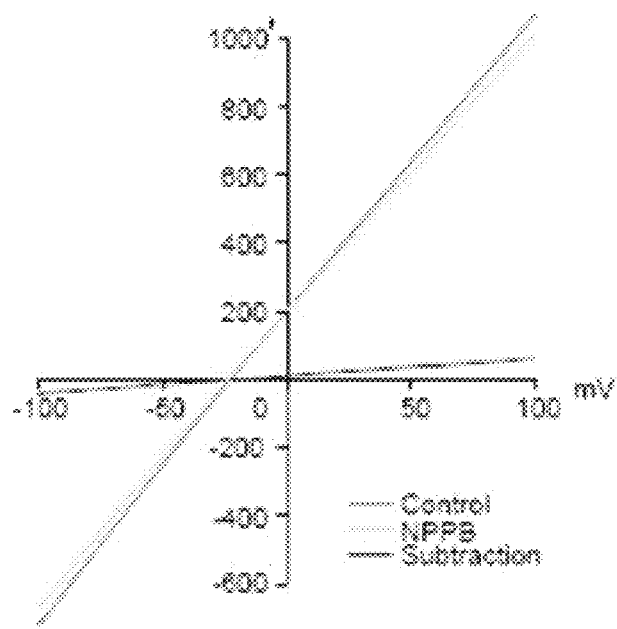
FIGS. 2e and 2f each shows current-voltage traces in GFAP-GFP mouse with scrambled shRNA injection and Best1-shRNA injection, respectively.
Figure 2F:
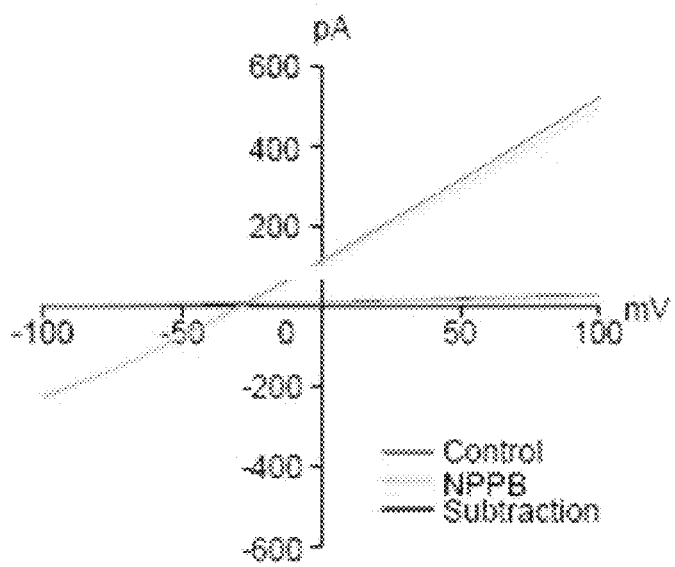

The whole-cell patch clamp recordings from Bergmann glial cells in cerebellar slice of naïve and lentivirus injected adult mice was performed to search for functional expression of Best1. The internal solution contained either mostly Cl⁻ or GABA as an anion, in addition to 4.5 μM free $Ca^{2+}$ to activate the endogenous Best1 channel. Anion current was isolated by subtracting the ramp current trace (from 100 mV to −100 mV in 2 s) during 50 μM NPPB application from that of baseline condition before NPPB application (FIG. 2d). The current-voltage relation of NPPB-sensitive anion current was generated for each cell by transforming the time in ramp trace to voltage (FIG. 2d, 2e, 2f). FIG. 2d shows Glial cell patch recording with ramp protocol (Vh=−70 mV). Anion current is decreased by anion channel blocker, NPPB (50 μM) in naïve GFAPGFP mice. Internal solution of GABA and Cl— are composed as indicated above. Current-voltage traces are generated from each ramp trace. Subtracted current represents NPPB sensitive current. FIGS. 2e and 2f show current-voltage traces in GFAP-GFP mouse with scrambled shRNA injection (2e) and Best1-shRNA injection (2f), respectively.

Figure 2G:
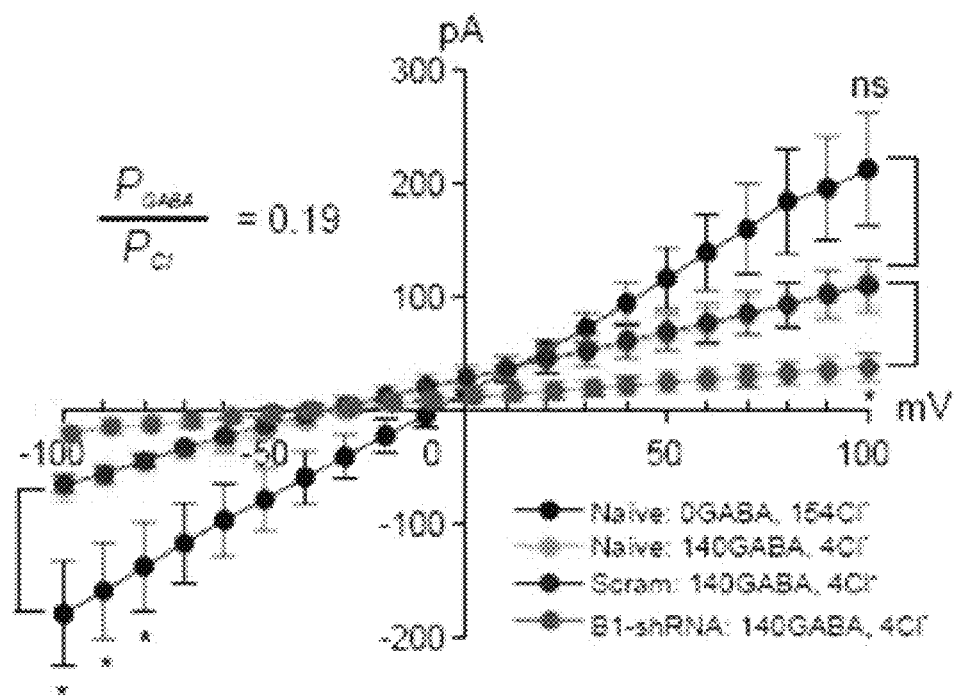
FIG. 2g illustrates the plotting of averaged current-voltage traces of NPPB sensitive current for each condition.

In FIG. 2g, current-voltage traces of NPPB sensitive current for each condition are averaged and plotted. GABA permeability is calculated using the reversal potential and Goldman-Hodgkin-Huxley equation. The NPPB-sensitive anion current under mostly Cl⁻ internal solution in naïve Bergmann glial cells showed averaged reversal potential of −6.9 mV (FIG. 2g, black trace, corrected for −3.5 mV junction potential), which was not very different from the calculated value from reversal potential of +1 mV using the Goldman-Hodgkin-Huxley equation and assuming a contribution of bicarbonate ($P_{HCO3}/P_{Cl}$=0.44; Qu and Hartzell, 2008). The GABA permeability ratio of NPPB-sensitive anioin current under GABA internal solution was similarly determined to be $P_{GABA}/P_{Cl}$=0.19 (FIG. 2g, green trace). The GABA permeability ratio obtained from naïve cells was not significantly different from that of scrambled-shRNA expressing Bergmann glial cells (FIG. 2g, blue trace). When the NPPB-sensitive current was isolated from Best1-shRNA expressing Bergmann glial cells, the conductance as indicated by the slope of the current-voltage trace decreased significantly without shifting the reversal potential (FIG. 2g, red trace)

Figure 2H:
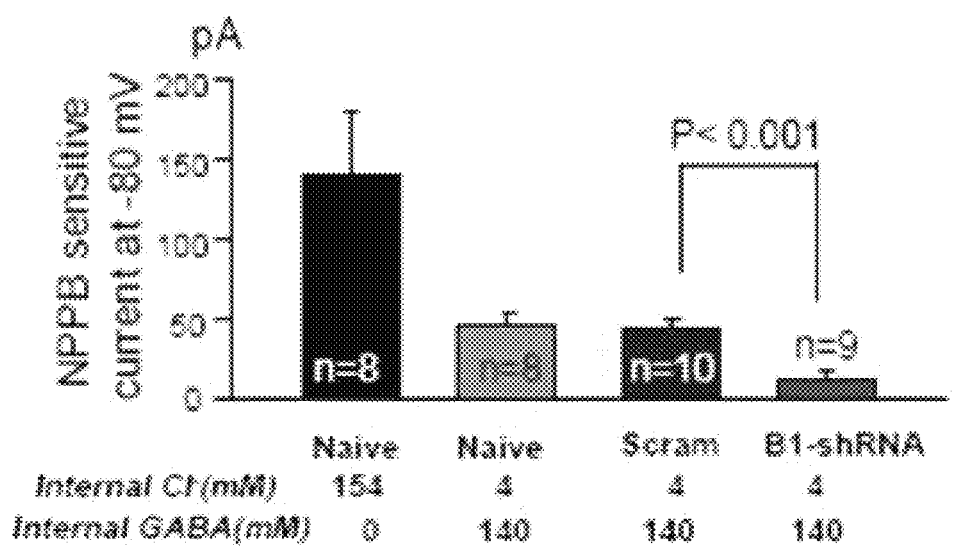
FIG. 2h represents the current amplitudes at −80 mV obtained from g to compare efflux of Cl⁻ and GABA

The outward current measured at 100 mV, which represents the Cl⁻ influx of did not show any significant difference between mostly Cl⁻ and GABA internal solution (212.23±49.52 pA (n=9), 112.52±20.93 pA (n=8), p=0.1), indicating that influx of Cl⁻ was not significantly affected by substitution of Cl⁻ to GABA internally. Both the inward current measured at −80 mV, which represents the efflux of GABA and outward current measured at 100 mV, which represents the influx of Cl⁻ under mostly GABA internal solution showed significant differences between the scrambled and Best1-shRNA cells (inward current: −44.62±5.01 pA (n=10), −12.99±5.92 pA (n=9), p<0.001, FIG. 2h; outward current: (110.26±23.25 pA (n=10), 38.31±12.02 pA (n=9), p=0.02).

These results indicate that NPPB-sensitive anion current observed in Bergmann glial cells is mostly mediated by Best1 channel, which displays a significant permeability to GABA at around resting membrane potential.

Example 5

Verification of GABA Release Inhibition by Best1 Silence 5.1: Virus injection

B6 wildtype, GFAP-GFP and hGFAP-CreERT2 trangenic mice (SPF room, Center for Neural Science, KIST, Seoul, Korea) were anaesthetized by intraperitoneal injection of 2% avertin (20 μl/g, sigma) and placed in a stereotaxic frame (David Kopf instrument). pSicoR-b1shRNA-mCherry or scrambled virus (Macrogen) was stereo-injected into cerebellar cortex at a rate of 0.2 μl/min (total 2 μl) using syringe pump (Harvard apparatus) and 25 μl syringe (Hamilton company). The coordination of injection site was 1.7 mm from the lambda and the depth was 1.5-1.7 mm from the skull.

5.2: Clomeleon Imaging

Figure 3A:
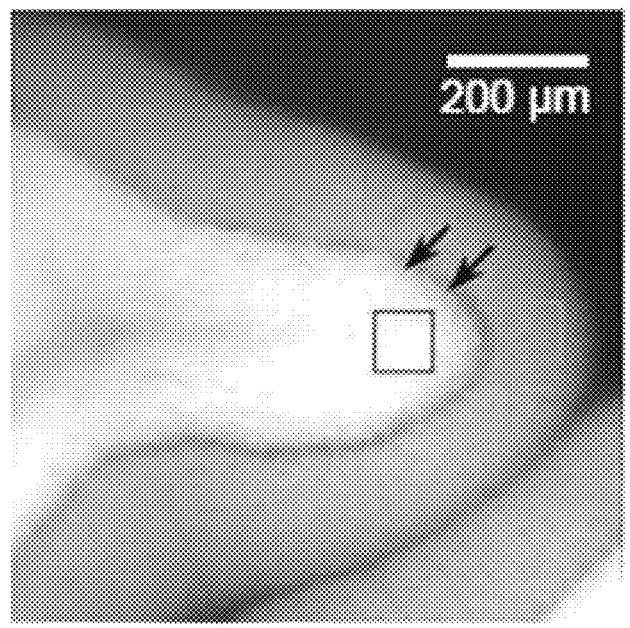

To test whether Best1 channel is responsible for tonic GABA release in cerebellum, an optogenetic approach was selected to assess $GABA_A$ receptor mediated $[Cl^-]_i$ movement in granule cells using the Thy1::CLM1 line (Department of Neurobiology, Duke University Medical Center, Durham, N.C., USA) of Clomeleon transgenic mice which show exclusive expression in granule cells in the cerebellum (FIG. 3a; Berglund and Augustine 2008).

FIG. 3a is a CFP-YFP FRET image representing cerebellar slice of CLM1 clomeleon mouse showing bright fluorescent granular cell bodies in granule cell layer and parallel fibers located in molecular layer, separated by translucent Purkinje cell layer (black arrows). Green and red squares indicate two regions of interest in molecular layer (green) and granule cell layer (red).

Clomeleon, based on fluorescence resonance energy transfer (FRET), is a genetically-encoded fluorescent indicator for Cl⁻ in which chloride-sensitive yellow fluroscent protein fused with chloride-insensitive cyan fluorescent protein via a flexible peptide linker (Kuner and Augustine, 2000). This Clomeleon mouse was successfully used to measure the tonic GABA release in cerebellar granule cells with added spatial information (Berglund et al).

Approximately 7-10 days after injecting pSicoR-b1shRNA-mCherry virus (Macrogrn) into the Clomelon transgenic mice, the cerebellar slices were prepared under the conventional methods. In brief, the brains were removed from the decapitated mice after anesthetizing with isoflurane and placed in a cold artificial cerebrospinal fluid (ACSF), containing (in mM): 125 NaCl, 2.5 KCl, 1.25 $NaH_2PO_4$, 26 $NaHCO_3$, 20 d(+)-glucose, 2 $CaCl_2$ and 1.3 $MgCl_2$ (pH 7.4 after bubbling with 95% $O_2$/5% $CO_2$, v/v). A vibratome (LEICA) was used to obtain 200 μm thick saggital section. The slices were then incubated at 36° C. for 30 min prior to use.

For imaging, two ROIs (Regions of Interest) covering the granule cell layer and the molecular layer were drawn. Excitation (440±10 nm) and emission (485±15 nm for CFP and 530±15 nm for YFP) filters (Cameleons 2 filter set 71007, Chroma Technologies, Rockingham, Vt.) were used. Fluorescence excitation was produced by two consecutive 200 to 500 ms long light pulses at 0.5 Hz and fluorescence emission was alternately collected at each wavelength with a back-illuminated, cooled CCD camera with the on-chip multiplication gain control (Cascade 512B, Photometrics). Image acquisition was controlled by RatioTool software (ISee Imaging Systems, Raleigh, N.C.) and a PowerMac G4 (Apple Computer).

Figure 3B:
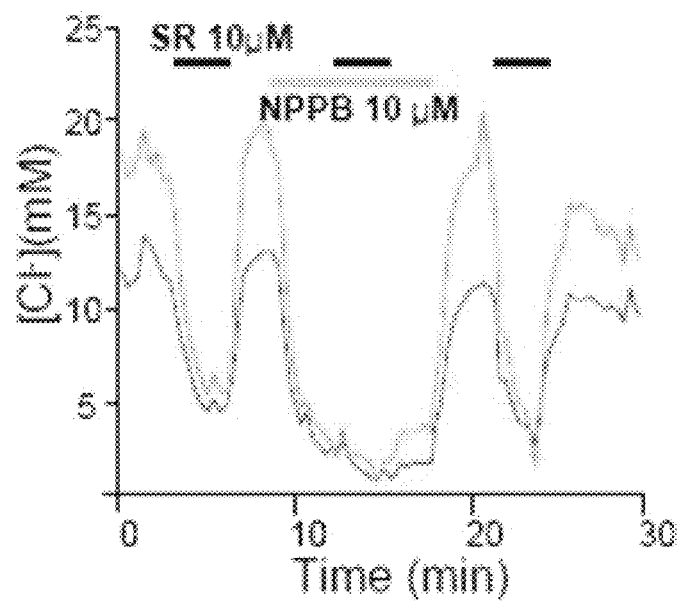

As expected, bath application of 10 μM GABAzine (SR95531) markedly decreased $[Cl^-]_i$ in granular cell bodies (FIG. 3b, red trace) and parallel fibers in molecular layer (FIG. 3b, green trace) as the block of extrasynaptic $GABA_A$ receptor decreased inward movement of $Cl^-$. Interestingly, the reduction was equally prominent in parallel fibers in molecular layer as in granular cell bodies (FIG. 3f). Application of 10 μM NPPB also decreased $[Cl^-]_i$ in both layers (FIG. 3b), indicating a decrease of tonic GABA. FIG. 3b shows ratiometric imaging of clomeleon illustrating the time course of $[Cl-]_i$ change. 10 μM SR (SR95531, or GABAzine) and anion channel blocker, NPPB (10 μM) decrease $[Cl]_i$.

Figure 3C:
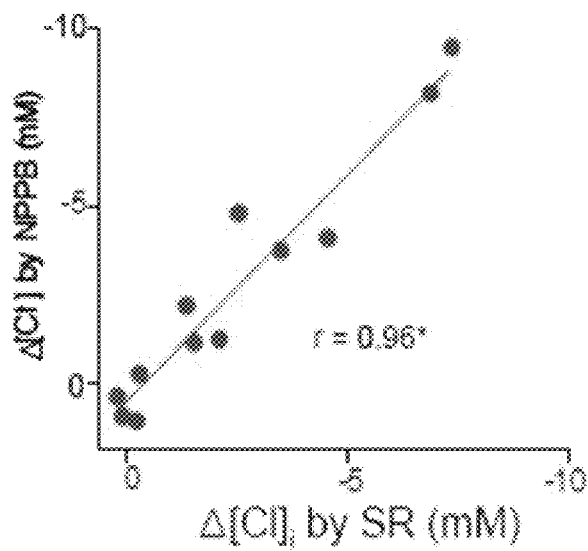

The degree of $[Cl^-]_i$ change by NPPB was closely correlated with change of $[Cl^-]_i$ by GABAzine (FIG. 3c, r=0.96). As shown in FIG. 3c, [Cl—]I change by NPPB is highly correlated with [Cl—]i change by SR.

Figure 3D:
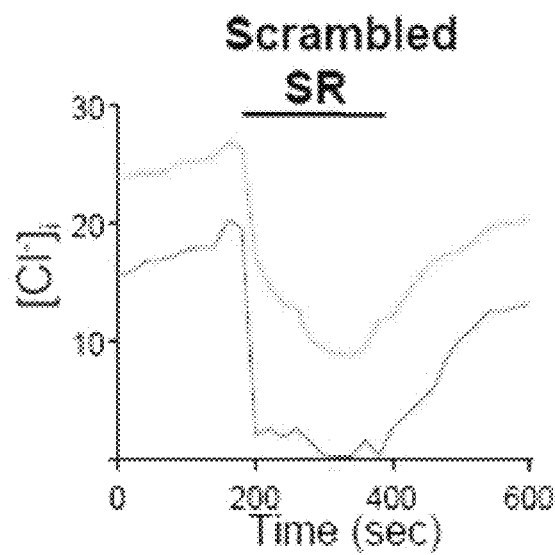
Figure 3E:
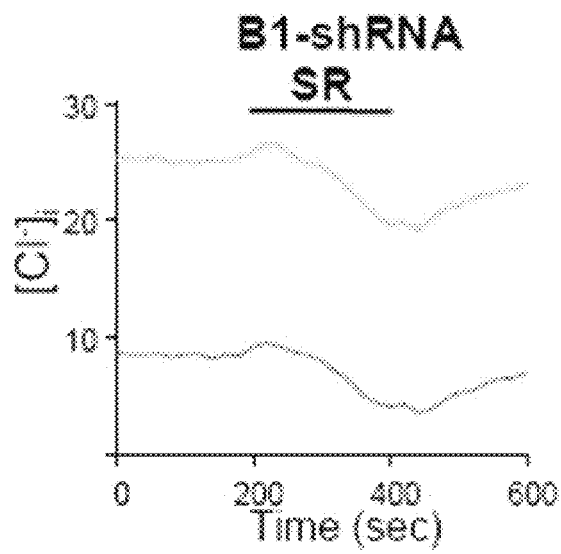
Figure 3F:
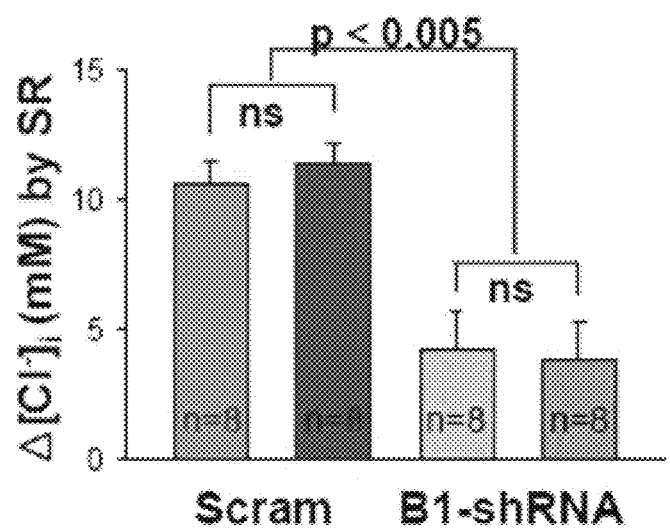

To test whether this $GABA_A$ receptor activation-induced $[Cl^-]_i$ change is Best1 channel dependent, $[Cl^-]_i$ concentration in granule cells of the Clomeleon mice with silenced Best1 gene was measured. $[Cl^-]_i$ concentration change by GABAzine was significantly decreased (FIG. 3e,f; p<0.005) in Best1-shRNA injected cerebellar slices (molecular layer: 10.63±1.45 mM, granule cell layer: 11.44±1.5 mM, (n=8)) compared to scrambled shRNA injected cerebellar slices (4.29±0.91 mM, 3.84±0.82 mM, (n=8)). FIG. 3f summarizes the $[Cl^-]_i$ changes due to scrambled shRNA injected cerebellar slices (FIG. 3d) and SR of Best1-shRNA injected cerebellar slices (FIG. 3e) (p<0.005). These results indicate that a gene silencing of Best1 channel reduces tonic GABA release detected in soma as well as in parallel fibers of granule cells.

5.3: The Whole-Cell Patch Clamp Recordings

Figure 3G:
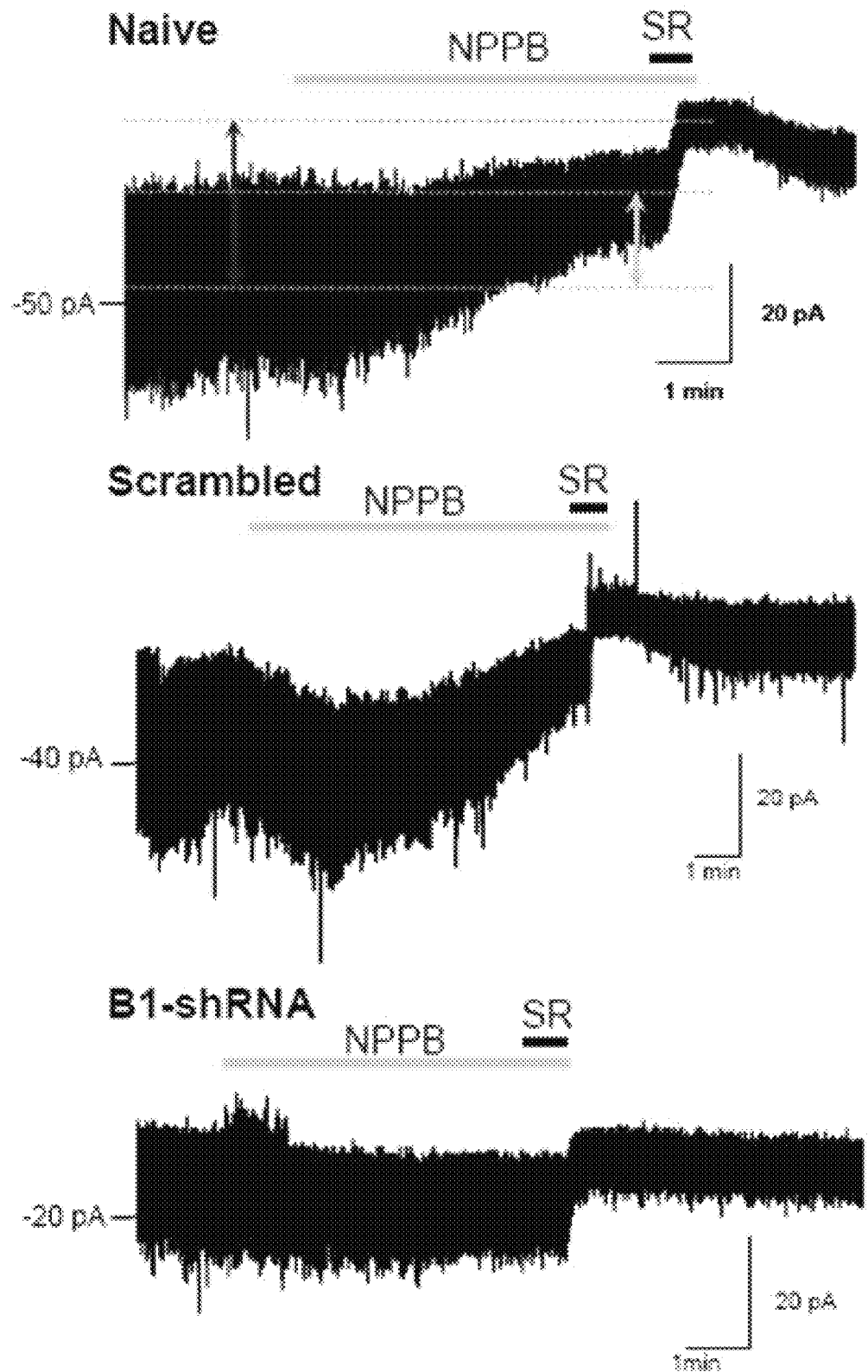

The results from Clomeleon mice were verified by the whole-cell patch clamp recordings in granule cells from adult mice injected with Best1-shRNA lentivirus. The GABAzine-sensitive current was significantly decreased in Best1-shRNA lentivirus injected mice (FIG. 3g lower panel, 8.28±0.57 pA, n=14) compared to those from naïve (35.68±4.05 pA (n=8), p<<0.001) or scrambled (26.62±2.85 pA (n=13), p<<0.001), whereas GABAzine-sensitive current between naïve and scrambled did not show any significant difference (p>0.09). The upper traces of FIG. 3g represents raw traces of tonic GABA current from granular cell in cerebellar slice (holding potential at −60 mV) of 8 wks B6 mice. Tonic GABA current is reduced by bath application of 50 μM NPPB. Blue arrow indicates GABAzine (SR) sensitive tonic GABA current and orange arrow indicates NPPB-sensitive tonic GABA current. Middle trace is related to a mouse injected with scrambled shRNA lentivirus and bottom trace is related a mouse injected with B1-shRNA lentivirus.

Figure 3H:
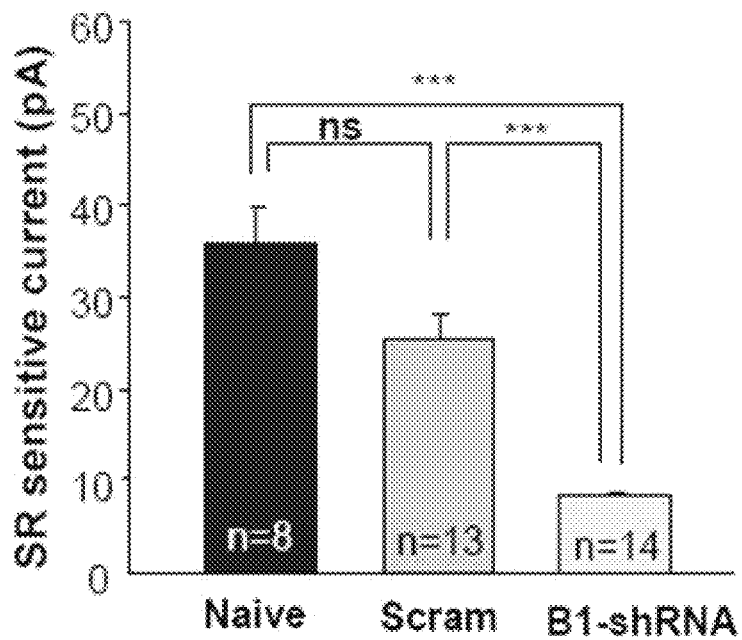
Figure 3I:
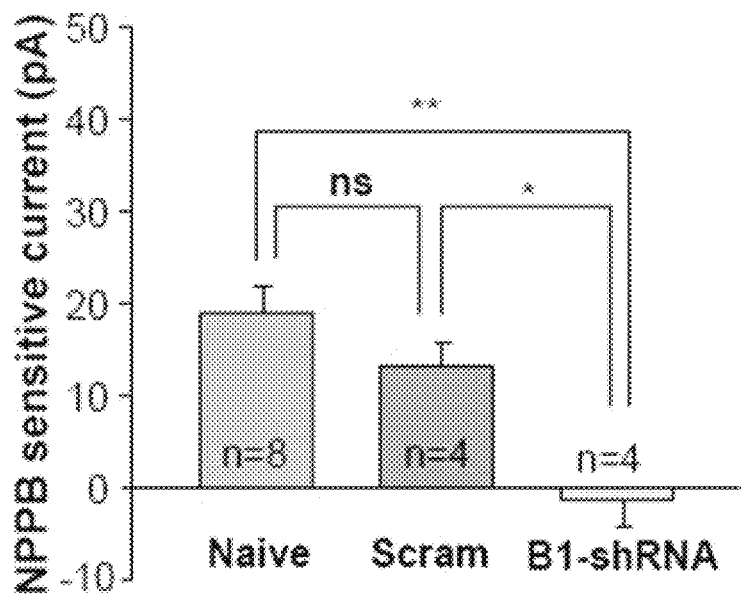

On the other hand, GABAzine-sensitive current did not show much difference between naive and scrambled mice (p>0.09, FIG. 3h). FIG. 3h is a summary figure of GABAzine-sensitive current from naive, scrambled, and B1-shRNA injected mice. The gene silencing of Best1 channel virtually eliminated the NPPB-sensitive component of tonic GABA current in Best1-shRNA injected mice (−1.23±3.08 pA, n=4), which showed a significant difference when compared to those in naive (18.95±2.47 pA (n=8), p<0.002) or scrambled mice (12.98±2.57 pA (n=4), p<0.02, n=4). FIG. 3i is a summary figure for NPPB sensitive current.

Figure 7A:
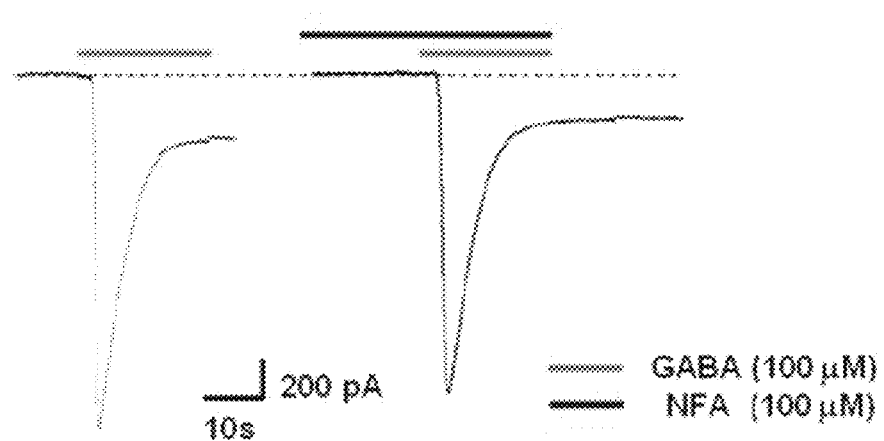
Figure 7B:
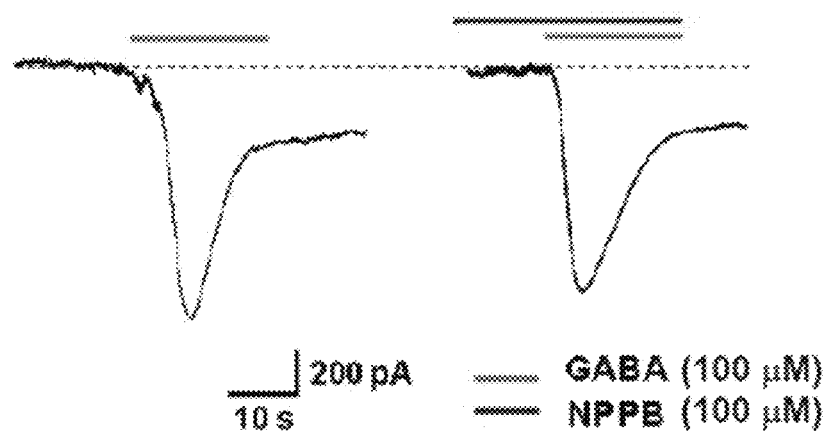
Figure 7C:
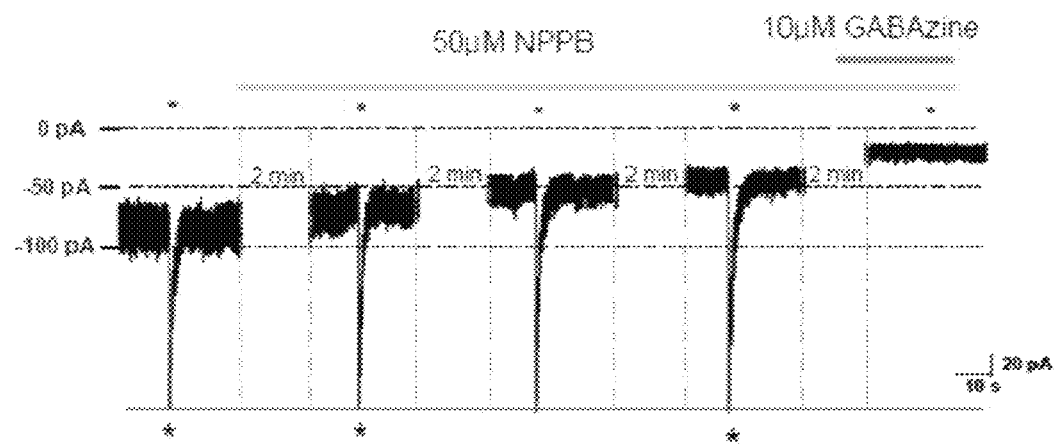
Figure 7D:
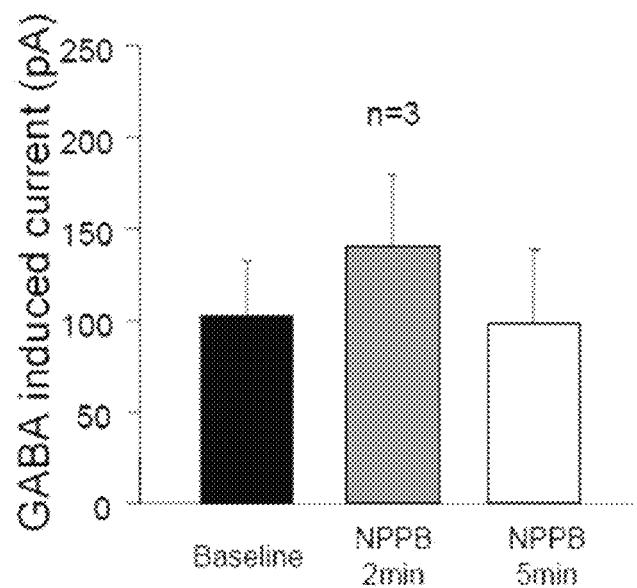

The inhibition of tonic GABA current caused by NPPB was not due to a direct action of this compound on $GABA_A$ receptor expressed in granule cells because NPPB did not have any effect on GABA-induced whole cell current (FIGS. 7c and 7d). FIGS. 7c and 7d shows that the application of NPPB in the wild B6 mouse did not affect GABA receptors in cerebellar granule cells. The magnitudes of GABA induced current with the NPPB application (2 and 5 min) are also shown.

Figure 6A:
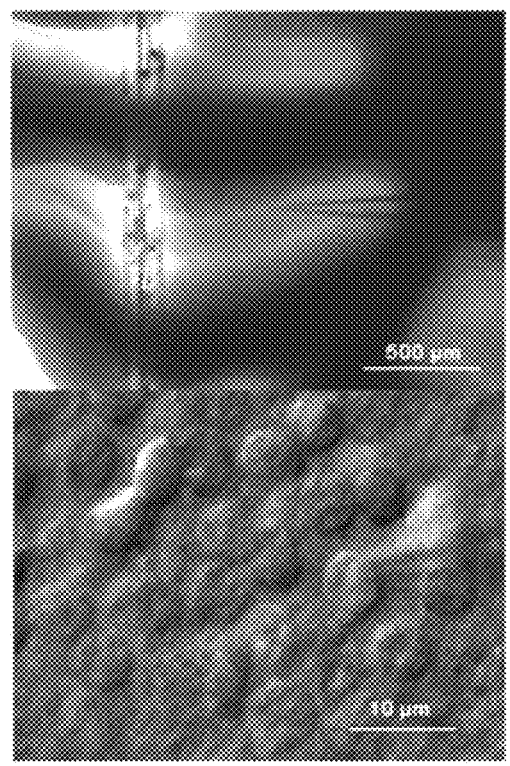
Figure 6B:
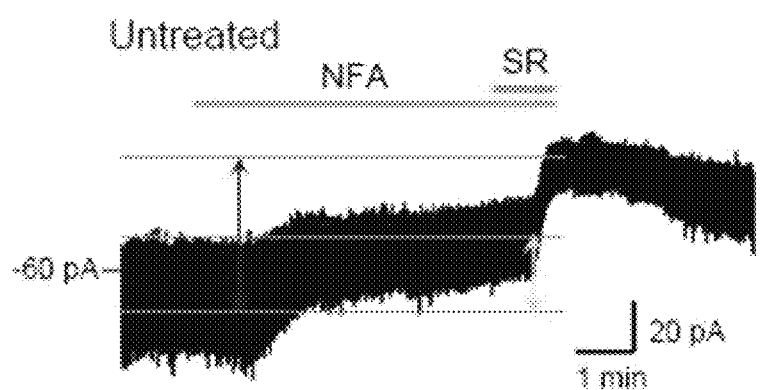

Other anion channel blockers, NFA and DIDS also blocked the GABAzine-sensitive current significantly (FIG. 6b,g). FIG. 5B shows the tonic GABA current recordings from granule cells when 100 μM Niflumic acid was applied. FIG. 5g indicates the block percentage of tonic current by $Ca^{2+}$ sensitive $Cl^-$ channel blockers. (The ages of mice used: 29.5±0.79, 27±0, 27.5±0.87, 28±0.71, and 74 days (DIDS)).

These results strongly support the idea that NPPB-sensitive tonic GABA release is mediated by Best1 channel in cerebellum and that the tonic GABA current is suppressed by the anion channel blockers as wells as Bestrophin channel gene silencing.

Example 6

Tonic GABA Current Recovery by Glia-specific Best1 Channel Rescue

In order to prevent the glia-specific Best1 from gene silencing, a test was done using hGFAP-CreERT2 mouse injected with tamoxifen and Best1-shRNA lentivirus to investigate whether tonic GABA release was due to glial Best1. (FIGS. 4a and 4b).

Figure 4A:
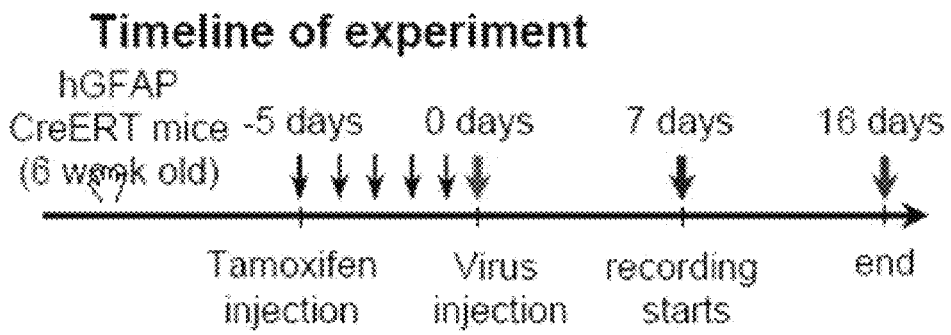
Figure 4B:
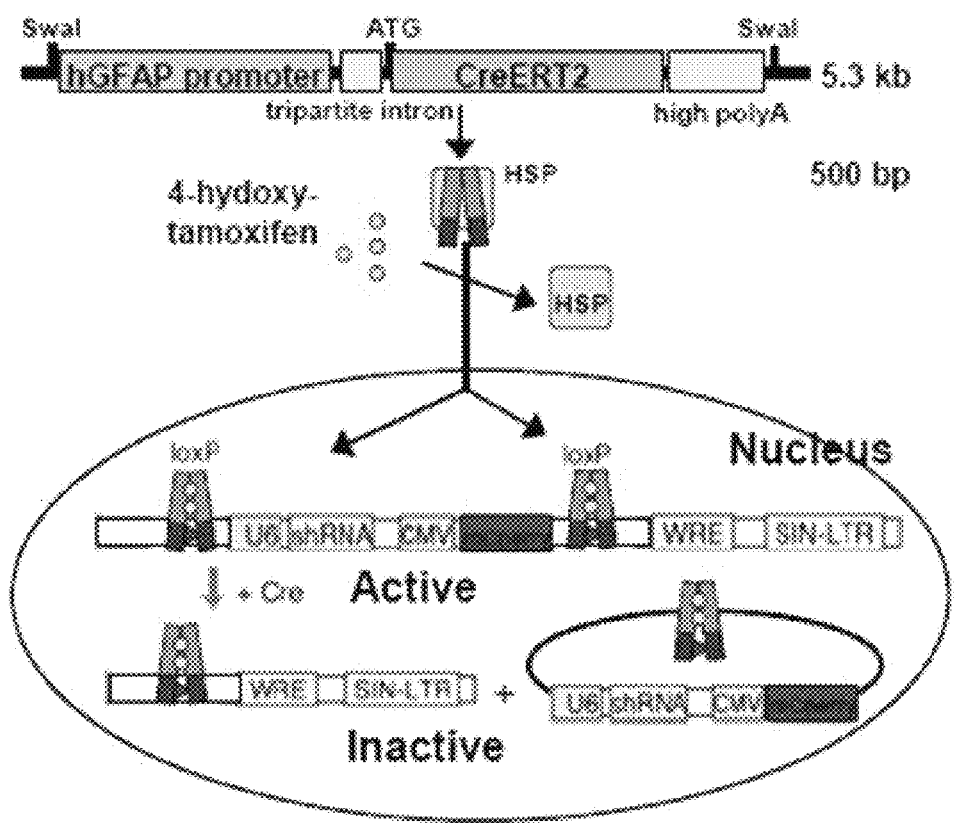

The glia-specific CreERT activation was initiated by intraperitoneal injection of tamoxifen for 5 days prior to lentivirus injection (FIG. 4a,b). FIG. 4a shows the experiment timeline for hGFAP-CreERT mice. Tamoxifen or sunflower oil were injected intraperitoncally once a day for 5 days before lentivirus injection. Under this strategy, the expressed CreERT was transferred to the nucleus to excise out the Best1-shRNA containing cassette, which then renders Best1-shRNA inactive (FIG. 4b). As shown in FIG. 4b, Cre-ERT was glia specifically expressed under GFAP promoter and activated by tamoxifen injection but inactivated by shRNA injection.

Figure 4C:
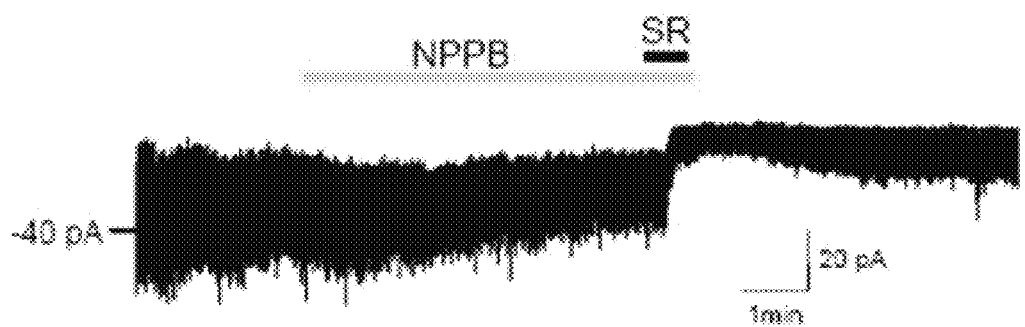
Figure 4C:
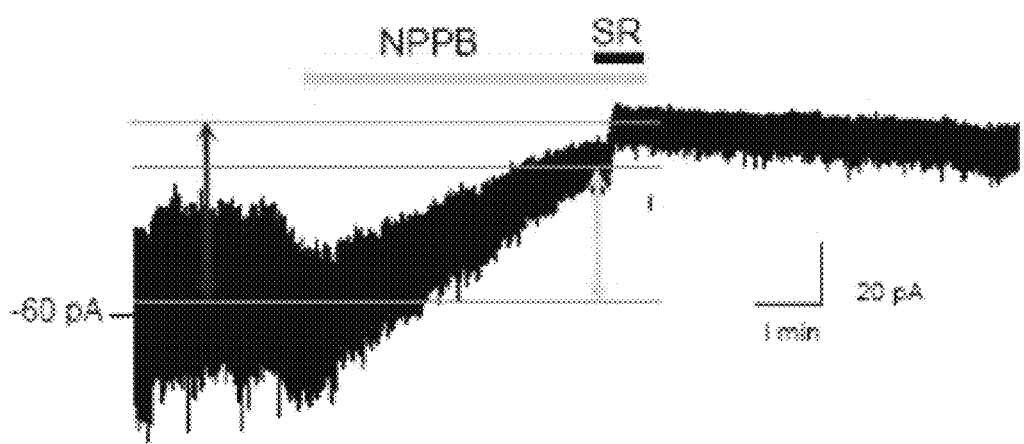
Figure 8B:
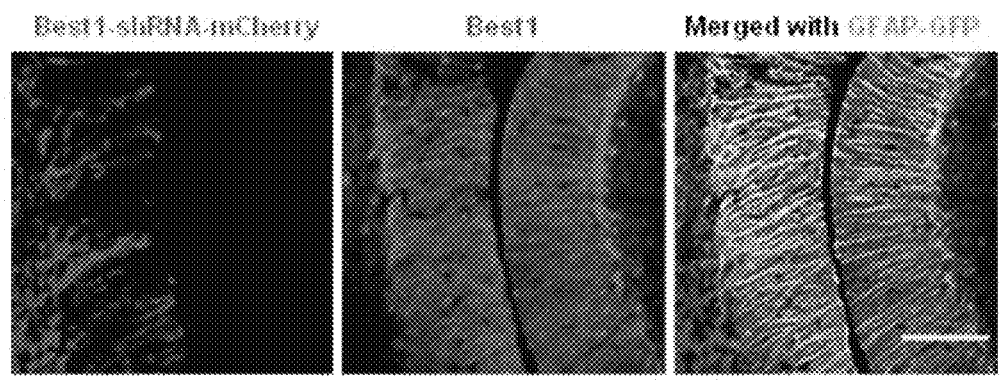
FIG. 8b shows the Best1 knock-down experiment due to gene silencing in hGFAP-Cre mouse. In the left panel, B1-shRNA lentivirus (red) is exhibited in the hGFAP-Cre mouse injected with tamoxifen. The middle panel shows Best1 stained image in the similar area. The right panel shows the image of GFAP (a marker for Glial cell) stained image in addition to the combined image of left and middle panel. Best1(red) indicates that lentivirus infected are is similarly stained as the non-infected area. (Scale bar; 100 μM).

The effect of glia specific rescue of Best1 was confirmed by immunohistochemistry with the Best1 antibody in either tamoxifen or sunflower oil injected hGFAP-CreERT2 mice (FIG. 8b). FIG. 4c shows the whole-cell patch clamp recording from granular cells. The upper trace shows tonic GABA current from hGFAP-CreERT mice injected with B1-shRNA lentivirus after sunflower oil treatment whereas the lower left, raw trace indicates tonic GABA current from hGFAP-Cre-ERT mice injected with B1-shRNA lentivirus after tamoxifen treatment. In the hGFAP-CreERT2 mice treated with sunflower oil and injected with Best1-shRNA lentivirus, GABAzine-sensitive current was significantly reduced (FIG. 4c, upper trace, 35.68±4.05 pA (naïve, n=8), 11.27±1.22 pA (with sunflower oil, n=9), p<0.003) to the similar level as that of wild type B6 mice injected with the same lentivirus (FIG. 3b). However, in the hGFAP-CreERT2 mice treated with tamoxifen and injected with Best1-shRNA lentivirus, GABAzine-sensitive currents were fully rescued to the naïve animal level (with Tamoxifen: 31.31±2.19 pA (n=8), naïve: 35.68±4.05 pA (n=12), p=0.36).

Figure 4D:
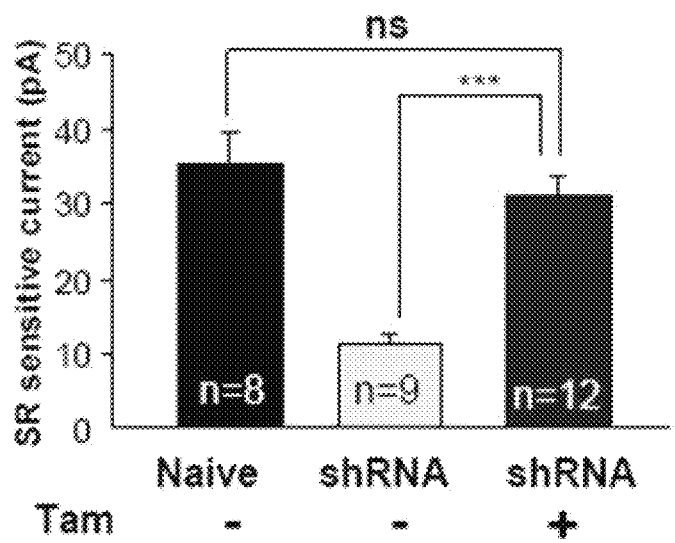
Figure 4E:
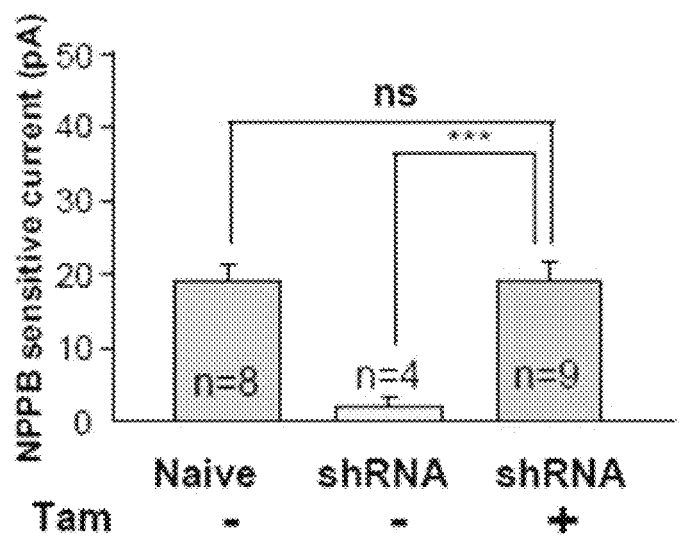

FIG. 4d shows the GABAzine-sensitive currents with and without Tamoxifen treatment. The GABAzine-sensitive currents with and without Tamoxifen treatment showed a significant difference (p<<0.001). FIG. 4e shows the NPPB-sensitive currents with and without Tamoxifen treatment. The NPPB-sensitive currents were fully rescued in the tamoxifen treated mice (naïve: 18.95±2.47 pA, n=8; with Tamoxifen: 19.27±2.2 pA n=9, p=0.93; without Tamoxifen: 1.93±1.56 pA, n=4, p=0.00005). These results indicate that glial Best1 channel is responsible for the majority of tonic GABA release detected in cerebellar granule cells.

Figure 6C:
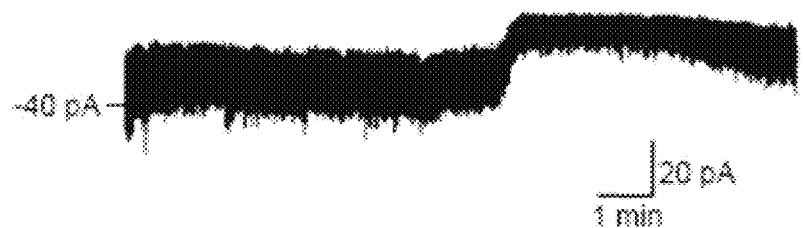
Figure 6D:
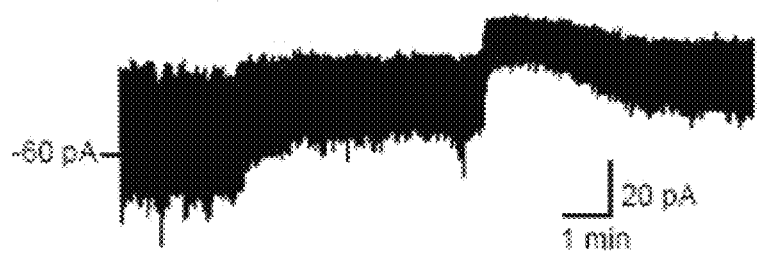
Figure 6E:
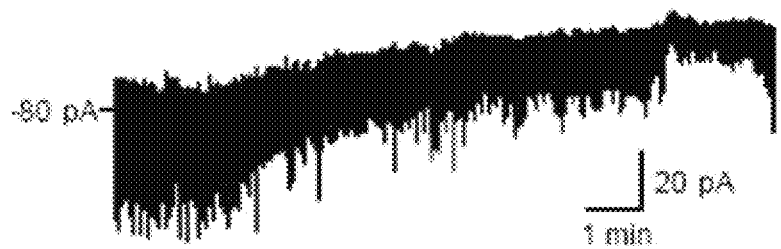
Figure 6F:
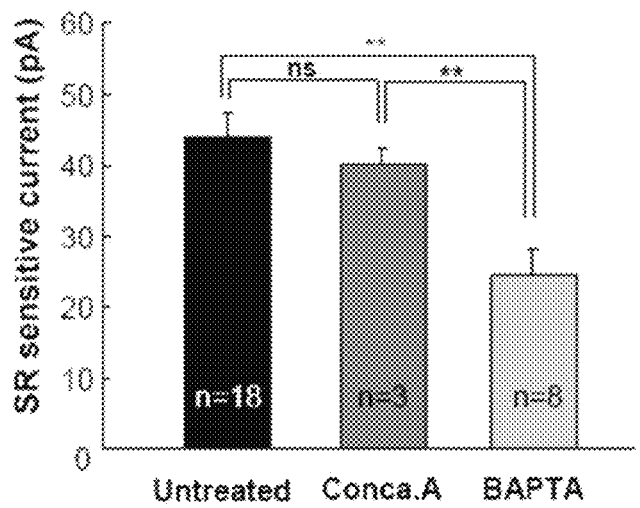
Figure 6G:
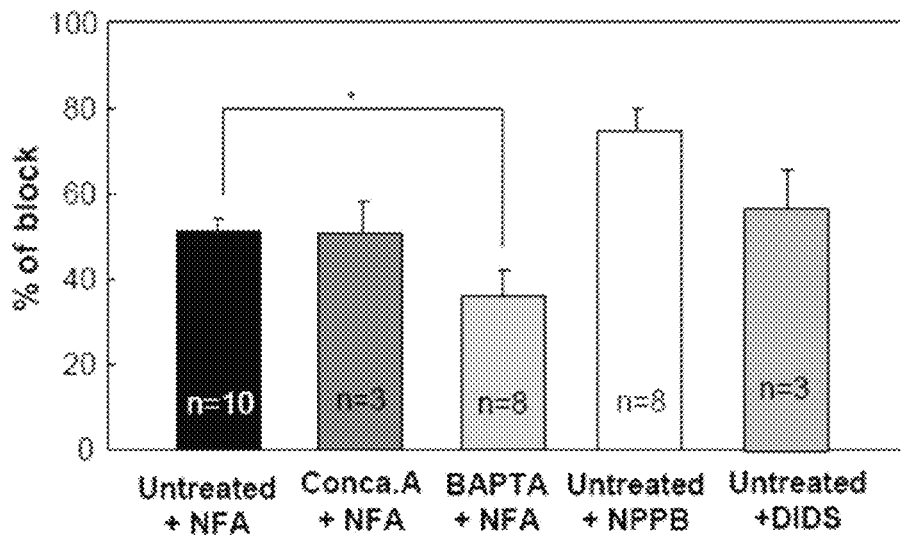

The amount of NPPB sensitive and Best1-mediated tonic GABA release is estimated to be about 70% of the total GABAzine-sensitive current. The source of remaining GABAzine sensitive, NPPB-insensitive or Best1-independent current is currently unknown and needs further investigation. Cloned Bestrophin channels are known to be activated at low $Ca^{2+}$ concentration range with apparent Kd for activation by $Ca^{2+}$ in the range of ~200 nM (Hartzell, et al, 2008). If native Best1 channel has the same $Ca^{2+}$ sensitivity, Best1 channels have to be partially activated at all times, because basal free cytosolic $Ca^{2+}$ is typically around 100 nM, resulting in a constitutive release of GABA through these channels. Consistent with this idea, chelating free cytosolic $Ca^{2+}$ with 25 min BAPTA-AM treatment significantly reduced the GABAzine-sensitive current (FIGS. 6c, 6d, 6f, and 6g). FIG. 6c shows the tonic GABA current when incubated with 150 µM of BAPTA-AM in granular cells. FIG. 6d shows the tonic GABA current when incubated with 0.5 µM of concanamycin A. As seen in FIG. 6c and 6d, the current dramatically decreased when treated with BAPTA-AM but concanamycin A did not have such affect. FIG. 6f shows GABAzine sensitive current with no treatment, concanamycin A-treatment, and BAPTA-AM treatment.

Figure 4F:
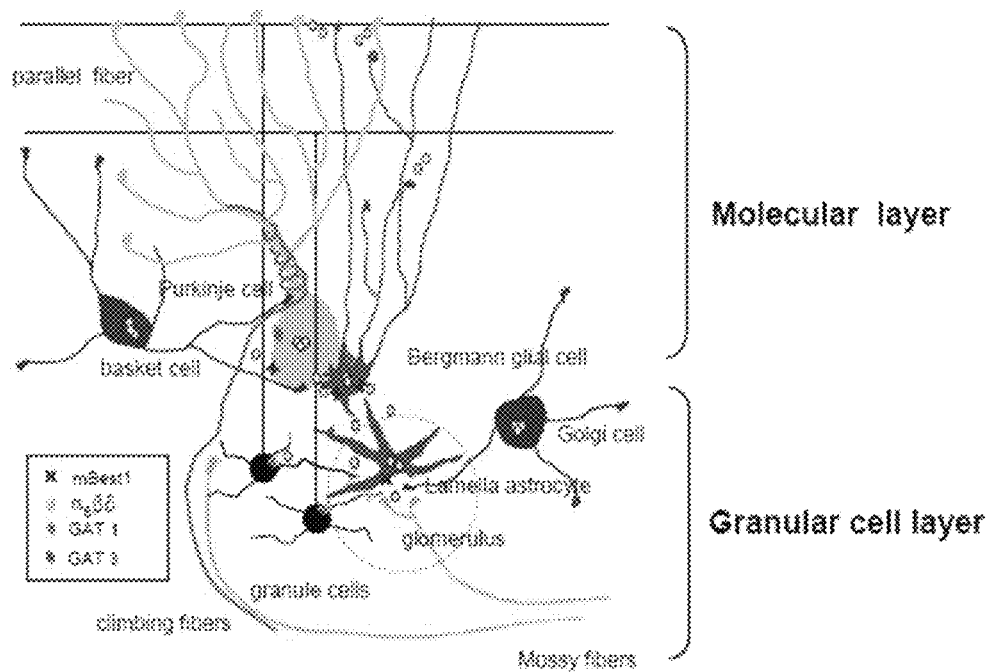

The results from the Clomeleon imaging suggest that tonic GABA can be readily detected from the parallel fibers in the molecular layer. GABA released from the neighboring Bergmann glial processes can serve a role as powerful inhibitor, profoundly affecting the local excitability of parallel fibers and synaptic release of glutamate onto the dendrites of Pukinje cells (FIG. 4f). FIG. 4f is a suggested model for tonic GABA release in cerebellum.

In summary, the present invention demonstrates an unprecedented mechanism of tonic GABA release through a recently characterized bestrophin channel in cerebellar glial cells, a unique role of anion channel in channel-mediated release of transmitter by direct permeation, and a novel glial function in releasing the major inhibitory transmitter GABA to modulate the neuronal excitability. The importance of this channel-mediated release of inhibitory gliotransmitter should provide further understanding of many unexplored physiological roles of glial cells in brain function.

What is claimed is:

1. A screening method for a cerebellar GABA release-regulating agent, said method comprising the steps of:
   preparing a cerebellar sample;
   contacting a candidate material to the cerebellar sample; and
   verifying the activation of Bestrophin 1 channel in the cerebellar sample,
   wherein said candidate material is determined to be a GABA release-promoting agent when the Bestrophin 1 channel is found to be activated, whereas the candidate material is determined to be a GABA release-inhibiting agent when the Bestrophin 1 channel is found to be inactivated.

2. The screening method according to claim 1, wherein the activation of Bestrophin 1 channel in cerebellar glial cells is verified.

3. The screening method according to claim 1, wherein the activation of Bestrophin 1 channel is verified by the measurement of an inward current change using sniffer patch technique.

* * * * *

SEQUENCE LISTING

<160> NUMBER OF SEQ ID NOS: 7

<210> SEQ ID NO 1
<211> LENGTH: 1904
<212> TYPE: DNA
<213> ORGANISM: Artificial Sequence
<220> FEATURE:
<223> OTHER INFORMATION: mouse Bestrophin 1 gene (NM_011913)

<400> SEQUENCE: 1

```
gacccaagcc cacctactgc tgcccagtgc caagccatga ctatcaccta cacaaacaaa     60
gtagccaatg cccgcctcgg ttcgttctcg tccctcctcc tgtgctggcg aggcagcatc    120
tacaagctgc tgtatggaga attccttgtc ttcatattcc tctactattc catccgtgga    180
ctctacagaa tggttctctc gagtgatcag cagctgttgt ttgagaagct ggctctgtac    240
tgcgacagct acatccagct catccctata tccttcgttc tgggtttcta tgttacattg    300
gtggtgagcc gctggtggag ccagtacgag aacttgccgt ggcccgaccg cctcatgatc    360
caggtgtcta gcttcgtgga gggcaaggat gaggaaggcc gtttgctgcg gcgcacgctc    420
atccgctacg ccatcctggg ccaagtgctc atcctgcgca gcatcagcac ctcggtctac    480
aagcgctttc ccactcttca ccacctggtg ctagcaggtt ttatgaccca tggggaacat    540
aagcagttgc agaagttggg cctaccacac aacacattct gggtgccctg ggtgtggttt    600
gccaacttgt caatgaaggc ctatcttgga ggtcgaatcc gggacaccgt cctgctccag    660
agcctgatga atgaggtgtg tactttgcgt actcagtgtg gacagctgta tgcctacgac    720
tggataagta tcccattggt gtacacacag gtggtgacag tggcagtata cagcttttc    780
```

```
cttgcatgct tgatcgggaa gcagtttctg aacccaaaca aggactaccc aggccatgag      840
atggatctgg ttgtgcctgt cttcacaatc ctgcaattct tattctacat gggctggctg      900
aaggtggcag aacagctcat caaccccttc ggggaggacg atgatgattt tgagactaac      960
tggatcattg acagaaacct gcaggtgtcc ctgttgtccg tggatgggat gcaccagaac     1020
ttgcctccca tggaacgtga catgtactgg aacgaggcag cgcctcagcc gccctacaca     1080
gctgcttctg ccaggtctcg ccggcattcc ttcatgggct ccaccttcaa catcagccta     1140
aagaaagaag acttagagct ttggtcaaaa gaggaggctg acacggataa gaaagagagt     1200
ggctatagca gcaccatagg ctgcttctta ggactgcaac ccaaaaacta ccatcttccc     1260
ttgaaagact aaagaccaa actattgtgt tctaagaacc ccctcctcga aggccagtgt      1320
aaggatgcca accagaaaaa ccagaaagat gtctggaaat ttaagggtct ggacttcttg     1380
aaatgtgttc caaggtttaa gaggagaggc tcccattgtg gcccacaggc acccagcagc     1440
caccctactg agcagtcagc accctccagt tcagacacag gtgatgggcc ttccacagat     1500
taccaagaaa tctgtcacat gaaaaagaaa actgtggagt ttaacttgaa cattccagag     1560
agccccacag aacatcttca acagcgccgt ttggaccaga tgtcaaccaa tatacaggct     1620
ctaatgaagg agcatgcaga gtcctatccc tacagggatg aagctggcac caaacctgtt     1680
ctctatgagt gatgcctcac agcctggccc tgacttgcaa ggatgcccag cagggcactg     1740
acccagtcaa aggcacacaa gcagcgacac ccaggagtgt gttcccacga cagtctagca     1800
tgtaactcag aaccaagagt acttaatagt cctgcctgaa aacacctgta ttttacgatc     1860
tttcccaaac taaggagttt aataaacgtg aatattcttt tagg                      1904
```

<210> SEQ ID NO 2
<211> LENGTH: 2673
<212> TYPE: DNA
<213> ORGANISM: Artificial Sequence
<220> FEATURE:
<223> OTHER INFORMATION: Human bestrophin 1 gene (NM_004183)

<400> SEQUENCE: 2

```
cagggagtcc caccagccta gtcgccagac cttctgtggg atcatcggac ccacctggaa       60
ccccacctga cccaagccca cctgctgcag cccactgcct ggccatgacc atcacttaca      120
caagccaagt ggctaatgcc cgcttaggct ccttctcccg cctgctgctg tgctggcggg      180
gcagcatcta caagctgcta tatggcgagt tcttaatctt cctgctctgc tactacatca      240
tccgctttat ttataggctg gccctcacgg aagaacaaca gctgatgttt gagaaactga      300
ctctgtattg cgacagctac atccagctca tccccatttc cttcgtgctg ggcttctacg      360
tgacgctggt cgtgacccgc tggtggaacc agtacgagaa cctgccgtgg cccgaccgcc      420
tcatgagcct ggtgtcgggc ttcgtcgaag gcaaggacga gcaaggccgg ctgctgcggc      480
gcacgctcat ccgctacgcc aacctgggca acgtgctcat cctgcgcagc gtcagcaccg      540
cagtctacaa gcgcttcccc agcgcccagc acctggtgca agcaggcttt atgactccgg      600
cagaacacaa gcagttggag aaactgagcc taccacacaa catgttctgg gtgccctggg      660
tgtggttttgc caacctgtca atgaaggcgt ggcttggagg tcgaatccgg accctatcc      720
tgctccagag cctgctgaac gagatgaaca ccttgcgtac tcagtgtgga cacctgtatg      780
cctacgactg gattagtatc ccactggtgt atacacaggt ggtgactgtg gcggtgtaca      840
gcttcttcct gacttgtcta gttgggcggc agtttctgaa cccagccaag gcctaccctg      900
```

```
gccatgagct ggacctcgtt gtgcccgtct tcacgttcct gcagttcttc ttctatgttg    960
gctggctgaa ggtggcagag cagctcatca accccttttgg agaggatgat gatgattttg  1020
agaccaactg gattgtcgac aggaatttgc aggtgtccct gttggctgtg gatgagatgc  1080
accaggacct gcctcggatg gagccggaca tgtactggaa taagcccgag ccacagcccc  1140
cctacacagc tgcttccgcc cagttccgtc gagcctcctt tatgggctcc accttcaaca  1200
tcagcctgaa caaagaggag atggagttcc agcccaatca ggaggacgag gaggatgctc  1260
acgctggcat cattggccgc ttcctaggcc tgcagtccca tgatcaccat cctcccaggg  1320
caaactcaag gaccaaacta ctgtggccca gagggaatc ccttctccac gagggcctgc   1380
ccaaaaacca caaggcagcc aaacagaacg ttaggggcca ggaagacaac aaggcctgga  1440
agcttaaggc tgtggacgcc ttcaagtctg ccccactgta tcagaggcca ggctactaca  1500
gtgccccaca gacgcccctc agccccactc ccatgttctt cccctagaa ccatcagcgc   1560 cgtcaaagct tcacagtgtc acaggcatag acaccaaaga caaaagctta agactgtga   1620 gttctggggc caagaaaagt tttgaattgc tctcagagag cgatgggcc ttgatggagc    1680 acccagaagt atctcaagtg aggaggaaaa ctgtggagtt taacctgacg gatatgccag  1740
agatccccga aaatcacctc aaagaacctt tggaacaatc accaaccaac atacacacta  1800
cactcaaaga tcacatggat ccttattggg ccttggaaaa cagggatgaa gcacattcct  1860
aacctgcttc ctaatgggga tgcttcgcca gccaggtcct cacctgtgtg tacaccagca  1920
ggacactgat ccagtcacag ccatacagct gtccacactg aagaacatgt cctacaacag  1980
cctgaatcaa atggttagct taatagataa aaatcccaga ctacttcagc ctttaatgcc  2040
ttttattcat aaaaactgtg aaagctagac tgaaccattg gaaacattta actcagactc  2100
tggattcaga gtcgggaacc cttagttcta tctgaatcca agcagccac accttagtat    2160 actgcccaaa ctaatgagtt taataaatac aaatactcgt ttcttttga ttagtgtgat   2220 tagaactgaa caacggcact taaggaatct ggaagatagc ctggatagat ttctgattca  2280
tcccaagacc tcaaagacaa cacctgggta ccaaatttct ttatttgaag gaatggtaca  2340
aatcaaagaa cttaagtgga tgttttggta caacttatag aaaaggtaaa ggaaccccca  2400
acatgcatgc actgccttgg tgaccaggga agtcaccca cggctatggg gaaattagcc    2460
cgaggcttag ctttcattat cactgtctcc cagggtgtgc ttgtcaaaga gatattccgc  2520
caagccagat tcgggcgctc ccatcttgcg caagttggtc acgtggtcac ccaattcttt  2580
gatggctttc acctgctcat tcaggtaatg tgtctcaatg aagtcacaca actgcaaaac  2640
aatggggaag acagttagtg ggcagctttc cca                               2673
```

<210> SEQ ID NO 3
<211> LENGTH: 60
<212> TYPE: DNA
<213> ORGANISM: Artificial Sequence
<220> FEATURE:
<223> OTHER INFORMATION: cDNA for shRNA (5'->3') for Best1 gene

<400> SEQUENCE: 3

```
gatcccttg ccaacttgtc aatgaattca agagattcat tgacaagttg gcaattttta     60
```

<210> SEQ ID NO 4
<211> LENGTH: 60
<212> TYPE: DNA
<213> ORGANISM: Artificial Sequence
<220> FEATURE:
<223> OTHER INFORMATION: cDNA for shRNA (3'->5') against Best1 gene

```
<400> SEQUENCE: 4
gggaacggtt gaacagttac ttaagttctc taagtaactg ttcaaccgtt aaaaattcga    60

<210> SEQ ID NO 5
<211> LENGTH: 20
<212> TYPE: DNA
<213> ORGANISM: Artificial Sequence
<220> FEATURE:
<223> OTHER INFORMATION: mBest1-F primer

<400> SEQUENCE: 5
aggacgatga tgattttgag                                                20

<210> SEQ ID NO 6
<211> LENGTH: 20
<212> TYPE: DNA
<213> ORGANISM: Artificial Sequence
<220> FEATURE:
<223> OTHER INFORMATION: mBest1-R primer

<400> SEQUENCE: 6
ctttctggtt tttctggttg                                                20

<210> SEQ ID NO 7
<211> LENGTH: 72
<212> TYPE: DNA
<213> ORGANISM: Artificial Sequence
<220> FEATURE:
<223> OTHER INFORMATION: artificial double-stranded oligonucleotide for
      lentivirus-based shRNA expression

<400> SEQUENCE: 7
cgctgcagtt gccaacttgt caatgaattc aagagattca ttgacaagtt ggcaattttt    60
gatatctaga ca                                                        72
```